United States Patent
Oh et al.

(10) Patent No.: US 8,617,789 B2
(45) Date of Patent: Dec. 31, 2013

(54) PHOTOACID GENERATOR, METHOD FOR PRODUCING THE SAME, AND RESIST COMPOSITION COMPRISING THE SAME

(75) Inventors: Jung Hoon Oh, Chungcheongnam-do (KR); Jin Bong Shin, Seoul (KR); Tae Gon Kim, Chungcheongnam-do (KR); Dong Chul Seo, Chungcheongnam-do (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 13/367,896

(22) Filed: Feb. 7, 2012

(65) Prior Publication Data

US 2012/0203024 A1    Aug. 9, 2012

(30) Foreign Application Priority Data

Feb. 7, 2011    (KR) .................. 10 2011 0010655

(51) Int. Cl.
     *C07C 69/76*      (2006.01)
     *G03F 7/004*      (2006.01)

(52) U.S. Cl.
     USPC ............ 430/270.1; 560/17; 560/73; 560/102; 560/111

(58) Field of Classification Search
     USPC ......................................... 560/17
     See application file for complete search history.

(56) References Cited

U.S. PATENT DOCUMENTS

| | | |
|---|---|---|
| 2004/0087690 A1 | 5/2004 | Lamanna et al. |
| 2010/0113818 A1 | 5/2010 | Oh et al. |

FOREIGN PATENT DOCUMENTS

| | | |
|---|---|---|
| EP | 2264007 A1 | 12/2010 |
| KR | 10-2010-0008336 | 1/2010 |

OTHER PUBLICATIONS

Tsuchimura, et al. Document No. 155:317112, retrieved from CAPLUS, Aug. 4, 2011.*
Search Report dated Apr. 17, 2013, issued by the Hungarian Intellectual Property Office on behalf of the Intellectual Property Office of Singapore for corresponding Singapore Patent Application No. 201200835-5.

\* cited by examiner

*Primary Examiner* — Shawquia Young
(74) *Attorney, Agent, or Firm* — Davidson, Davidson & Kappel, LLC

(57) ABSTRACT

A photoacid generator represented by the following formula (1), a method for producing the photoacid generator, and a resist composition containing the photoacid generator are provided.

[Chemical Formula 1]

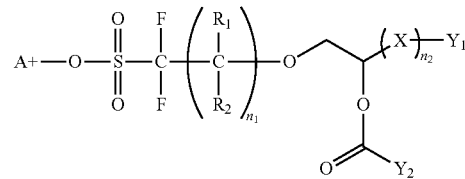

wherein in the formula (1), $Y_1$, $Y_2$, X, $R_1$, $R_2$, $n_1$, $n_2$ and $A^+$ have the same meanings as defined in the detailed description of the invention. The photoacid generator can maintain an appropriate contact angle at the time of ArF liquid immersion lithography, can reduce defects occurring during liquid immersion lithography, and has excellent solubility in resist solvents and excellent compatibility with resins. Furthermore, the photoacid generator can be produced by an efficient and simple method using an epoxy compound that is industrially easily available.

9 Claims, No Drawings

PHOTOACID GENERATOR, METHOD FOR PRODUCING THE SAME, AND RESIST COMPOSITION COMPRISING THE SAME

BACKGROUND OF THE INVENTION

1. Field of the Invention

The present invention relates to a photoacid generator, a method for producing the photoacid generator, and a resist composition containing the photoacid generator. More particularly, the present invention relates to a photoacid generator which can maintain an appropriate contact angle at the time of ArF liquid immersion lithography, can reduce the defects occurring during liquid immersion lithography, has excellent solubility in resist solvents and excellent compatibility with resins, and can be produced by an efficient and simple method using an industrially easily available epoxy compound, a method for producing the photoacid generator, and a resist composition containing the photoacid generator.

2. Description of the Related Art

Chemically amplified positive resist compositions that are used in the semiconductor microprocessing including a lithographic process, include an acid generator containing a compound which generates acid when irradiated with light.

The acid generator absorbs the light used in semiconductor patterning processes. Onium salts that are mainly used as acid generators are such that the cationic moiety is decomposed into a radical form and comes to exist as a molecule of another form, and the anionic moiety generates acid, so that after irradiation, diffusion occurs on the resist film at the time of baking of the wafer.

During this process, the acid generator directly affects the resolution of the resist, the line edge roughness and the like by means of various factors such as the ability to absorb light, the acid production efficiency for the acid produced as a result of light absorption, the diffusion capability of the acid generated from the anion, and the strength of the acid generated from the anion.

Furthermore, in order to obtain excellent smoothness, the acid generator used in such chemically amplified resist materials needs to be uniformly dispersed in the resist composition. Therefore, the solubility of acid generators in resist solvents and compatibility thereof with resins are very important. However, conventional photoacid generators are not excellent in the solubility in solvents and the compatibility with resins, it is difficult to produce photoacid generators at low cost.

SUMMARY OF THE INVENTION

Accordingly, it is an object of the present invention to provide a photoacid generator which can maintain an appropriate contact angle at the time of ArF liquid immersion lithography, can reduce the defects occurring during liquid immersion lithography, and has excellent solubility in resist solvents and excellent compatibility with resins.

Another object of the present invention is to provide a method for producing the photoacid generator described above.

Another object of the present invention is to provide a resist composition containing the photoacid generator described above.

According to an aspect of the present invention, there is provided a photoacid generator represented by the following formula (1):

[Chemical Formula 1]

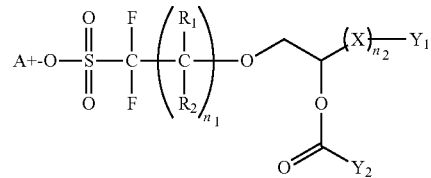

wherein in the formula (1), $Y_1$ and $Y_2$ each independently represent any one selected from the group consisting of an alkyl group, an alkenyl group, an alkoxy group, a cycloalkyl group, a heterocycloalkyl group, an aryl group and a heteroaryl group; X represents any one selected from the group consisting of an alkanediyl, an alkenediyl, NR', S, O, CO and combinations thereof; R' represents any one selected from the group consisting of a hydrogen atom and an alkyl group; $R_1$ and $R_2$ each independently represent a hydrogen atom, an alkyl group, an alkoxy group, a perfluoroalkyl group, a perfluoroalkoxy group, a halogen group, a hydroxyl group, a carboxyl group, a cyano group, a nitro group, an amino group and a thio group; $n_1$ represents an integer from 1 to 2; $n_2$ represents an integer from 0 to 5; and $A^+$ represents an organic counterion.

$Y_1$ and $Y_2$ may be each independently any one selected from the group consisting of an alkyl group, an alkenyl group, an alkoxy group, a cyclopentyl group, a cyclohexyl group, a decahydronaphthalene group, an octahydro-1H-indene group, an adamantyl group, a norbornyl group, a tetrahydrofuran group, a polycyclic cycloalkyl group containing a norbornyl group having 10 to 30 carbon atoms, a phenyl group, a naphthyl group, a biphenyl group, an anthryl group, a penanthrene group, a fluorenyl group, a pyrene group, a phenalene group, an indene group, a biphenylene group, a diphenylmethyl group, a tetrahydronaphthyl group, a dihydroanthryl group, a tetraphenylmethyl group, and a triphenylmethyl group.

Y may be any one selected from the group consisting of an alkyl group, an alkenyl group, an alkoxy group, and groups represented by the following formulas (1-a) to (1-i) and formulas (2-a) to (2-l):

[Chemical Formula 1-a]

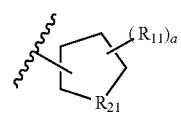

[Chemical Formula 1-b]

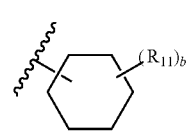

[Chemical Formula 1-c]

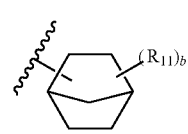

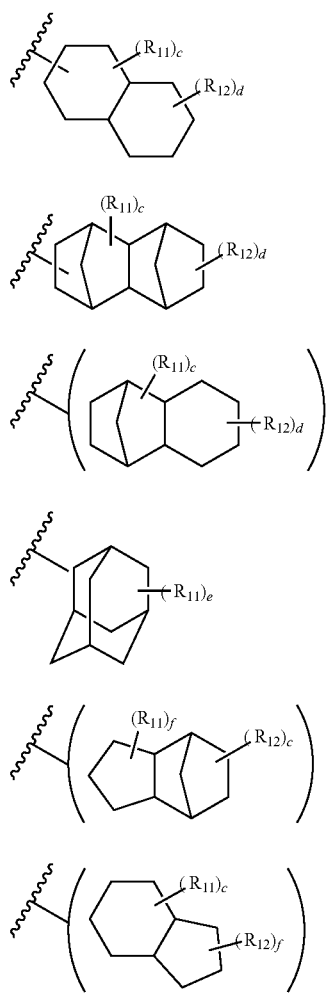

[Chemical Formula 1-d]

[Chemical Formula 1-e]

[Chemical Formula 1-f]

[Chemical Formula 1-g]

[Chemical Formula 1-h]

[Chemical Formula 1-i]

wherein in the formulas (1-a) to (1-i), $R_{11}$ and $R_{12}$ each independently represent any one selected from the group consisting of a hydrogen atom, an alkyl group, an alkoxy group, a perfluoroalkyl group, a perfluoroalkoxy group, a halogen atom, a hydroxyl group, a carboxyl group, a cyano group, a nitro group, an amino group, a thio group, a methylthio group, a methoxy group; OR', COR', COOR', O and S; R' represents any one selected from the group consisting of an alkyl group and an aryl group; $R_{21}$ represents any one selected from the group consisting of $CR_{24}R_{25}$, O, CO, S and $NR_{23}$; $R_{23}$ to $R_{25}$ each independently represent any one selected from the group consisting of a hydrogen atom, an alkyl group and an aryl group; a, c and d each independently represent an integer from 0 to 9; b represents an integer from 0 to 11; e represents an integer from 0 to 15; f represents an integer from 0 to 7; $0 \leq c+d \leq 17$; and $0 \leq c+f \leq 15$.

[Chemical Formula 2-a]

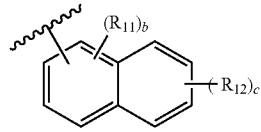

[Chemical Formula 2-b]

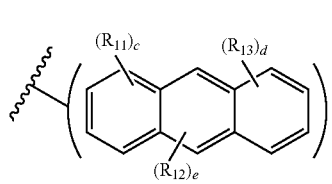

[Chemical Formula 2-c]

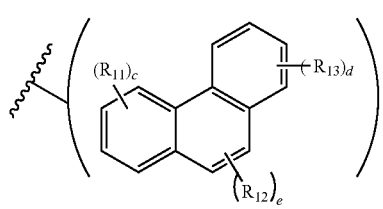

[Chemical Formula 2-d]

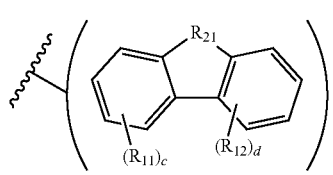

[Chemical Formula 2-e]

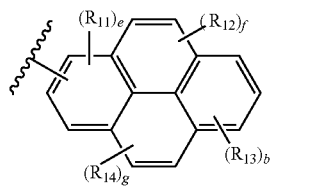

[Chemical Formula 2-f]

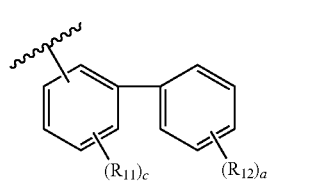

[Chemical Formula 2-g]

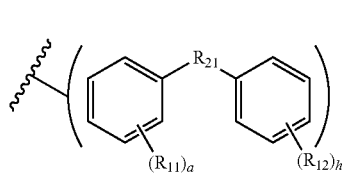

[Chemical Formula 2-h]

[Chemical Formula 2-i]

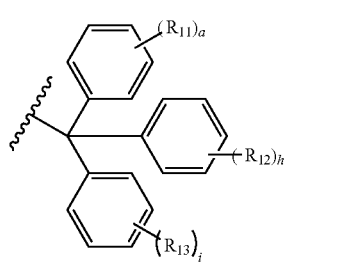

-continued

[Chemical Formula 2-j]

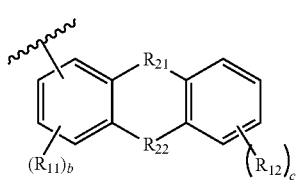

[Chemical Formula 2-k]

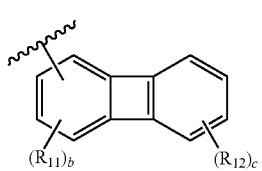

[Chemical Formula 2-l]

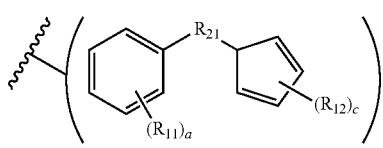

wherein in the formulas (2-a) to (2-l), $R_{11}$, $R_{12}$, $R_{13}$ and $R_{14}$ each independently represent any one selected from the group consisting of an alkyl group, an alkoxy group, a perfluoroalkyl group, a perfluoroalkoxy group, a halogen atom, a hydroxyl group, a cyano group, a nitro group, an amino group and a thio group; $R_{21}$ and $R_{22}$ each independently represent any one selected from the group consisting of $CR_{24}R_{25}$, O, CO, S and $NR_{23}$; $R_{23}$ to $R_{25}$ each independently represent any one selected from the group consisting of a hydrogen atom, an alkyl group, and an aryl group; a, h and i each independently represent an integer from 0 to 5; b represents an integer from 0 to 3; c and d each independently represent an integer from 0 to 4; e, f and g each independently represent an integer from 0 to 2; and $0 \leq c+d+e \leq 9$.

The photoacid generator may be any one selected from the group consisting of compounds represented by the following formulas (3-1) to (3-14):

[Chemical Formula 3-1]

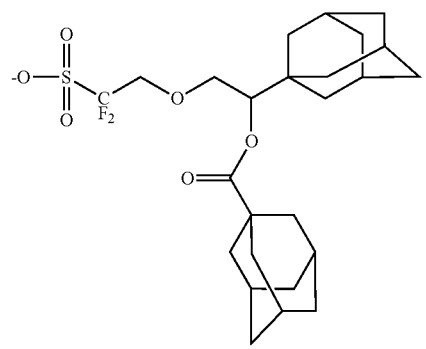

[Chemical Formula 3-2]

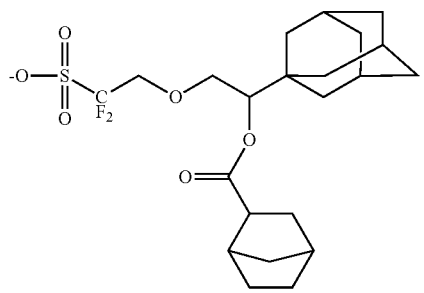

[Chemical Formula 3-3]

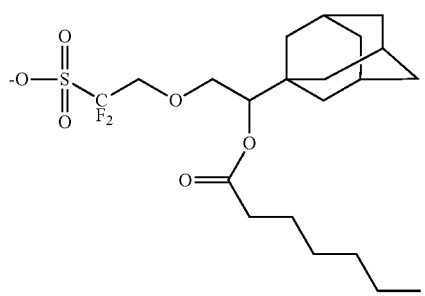

[Chemical Formula 3-4]

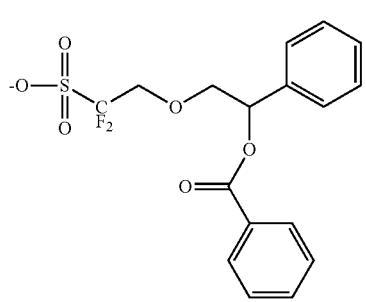

[Chemical Formula 3-5]

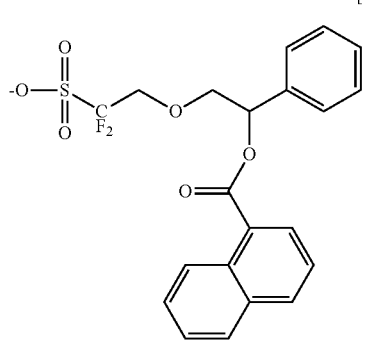

[Chemical Formula 3-6]

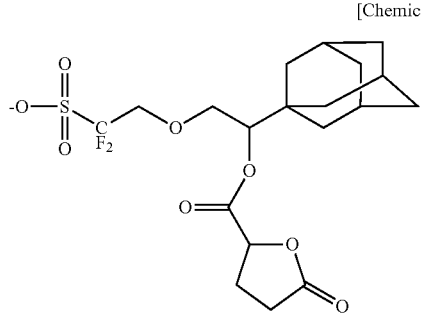

[Chemical Formula 3-7]

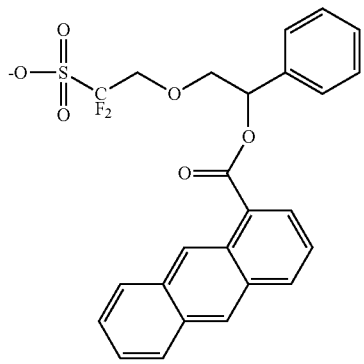

[Chemical Formula 3-8]

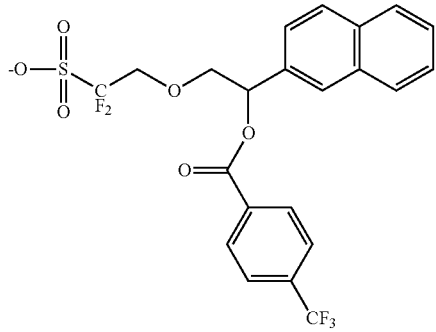

[Chemical Formula 3-9]

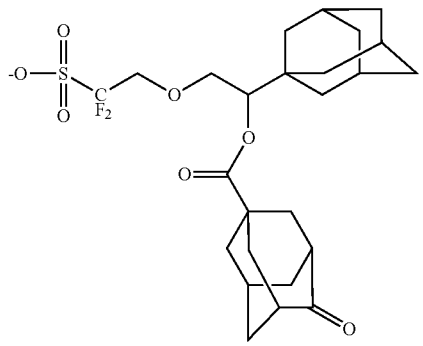

[Chemical Formula 3-10]

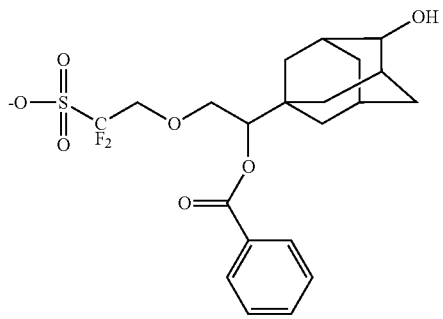

[Chemical Formula 3-11]

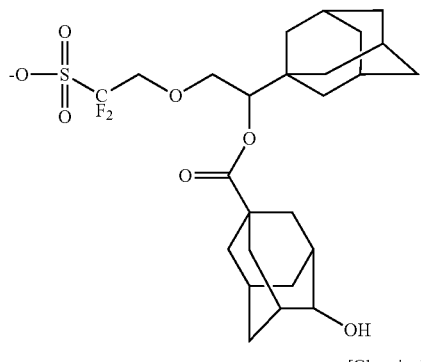

[Chemical Formula 3-12]

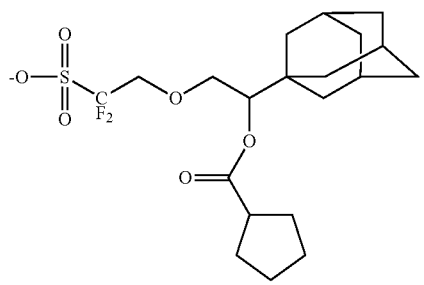

[Chemical Formula 3-13]

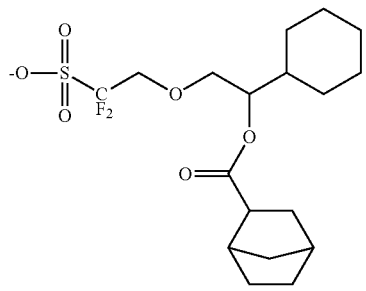

[Chemical Formula 3-14]

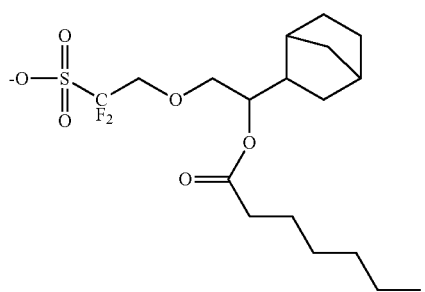

According to another aspect of the present invention, there is provided a method for producing a photoacid generator, including a first step of allowing a hydroxysulfonic acid salt to react with oxirane and thereby producing a hydroxyethoxysulfonic acid salt; a second step of allowing the hydroxyethoxysulfonic acid salt produced above to react with a carbonyl halide and thereby producing an intermediate; and a third step of subjecting the intermediate thus produced to a substitution reaction of the cation, and thereby producing a compound represented by the following formula (1):

[Chemical Formula 1]

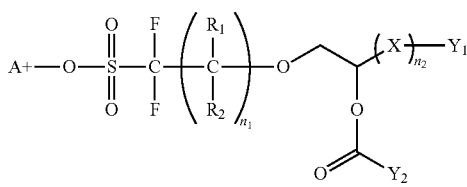

wherein in the formula (1), $Y_1$ and $Y_2$ each independently represent any one selected from the group consisting of an alkyl group, an alkenyl group, an alkoxy group, a cycloalkyl group, a heterocycloalkyl group, an aryl group and a heteroaryl group; X represents any one selected from the group consisting of an alkanediyl, an alkenediyl, S, O, CO and combinations thereof; R' represents any one selected from the group consisting of a hydrogen atom and an alkyl group; $R_1$ and $R_2$ each independently represent a hydrogen atom, an alkyl group, an alkoxy group, a perfluoroalkyl group, a perfluoroalkoxy group, a halogen group, a hydroxyl group, a carboxyl group, a cyano group, a nitro group, an amino group and a thio group; $n_1$ represents an integer from 1 to 2; $n_2$ represents an integer from 0 to 5; and $A^+$ represents an organic counterion.

The hydroxysulfonic acid salt may be represented by the following formula (6), the oxirane may be represented by the following formula (7), and the hydroxyethoxysulfonic acid salt may be represented by the following formula (8). The carbonyl halide may be represented by the following formula (9), and the intermediate may be represented by the following formula (10).

[Chemical Formula 6]

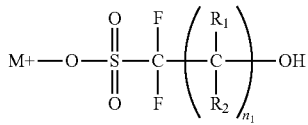

[Chemical Formula 7]

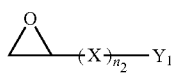

[Chemical Formula 8]

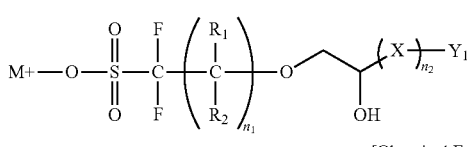

[Chemical Formula 9]

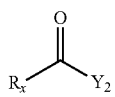

[Chemical Formula 10]

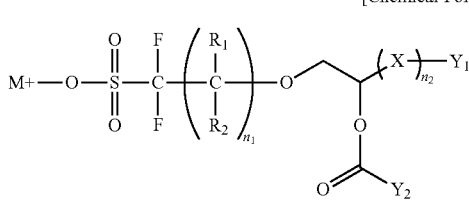

wherein in the formulas (6) to (10), $Y_1$ and $Y_2$ each independently represent any one selected from the group consisting of an alkyl group, an alkenyl group, an alkoxy group, a cycloalkyl group, a heterocycloalkyl group, an aryl group and a heteroaryl group; X represents any one selected from the group consisting of an alkanediyl, an alkenediyl, NR', S, O, CO and combinations thereof; R' represents any one selected from the group consisting of a hydrogen atom and an alkyl group; $R_1$ and $R_2$ each independently represent any one selected from the group consisting of a hydrogen atom, an alkyl group, an alkoxy group, a perfluoroalkyl group, a perfluoroalkoxy group, a halogen atom, a hydroxyl group, a carboxyl group, a cyano group, a nitro group, an amino group and a thio group; $R_x$ represents a halogen atom; $n_1$ represents an integer from 1 to 2; $n_2$ represents an integer from 0 to 5; and $M^+$ represents an alkali metal ion.

Any one step selected from the group consisting of the first step, the second step and a combination thereof may be carried out by allowing the reaction to proceed in the presence of any one catalyst selected from the group consisting of an acidic catalyst and a basic catalyst.

The second step may be carried out by allowing the hydroxyethoxysulfonic acid salt to react with the carbonyl halide for 1 to 12 hours at 20° C. to 100° C.

According to another aspect of the present invention, there is provided a resist composition containing the photoacid generator described above.

DESCRIPTION OF THE PREFERRED EMBODIMENTS

The definitions of the terms used in the present specification are as follows.

Unless particularly stated otherwise in the present specification, a halogen group means any one selected from the group consisting of fluorine, chloride, bromine and iodine.

Unless particularly stated otherwise herein, an alkyl group includes a primary alkyl group, a secondary alkyl group and a tertiary alkyl group.

Unless particularly stated otherwise herein, an alkanediyl means a divalent atomic group obtained by extracting two hydrogen atoms from an alkane, and can be represented by formula: —$C_nH_{2n}$—. An alkenediyl means a divalent atomic group obtained by extracting two hydrogen atoms from an alkene, and can be represented by formula: —$C_nH_n$—.

Unless particularly stated otherwise herein, a perfluoroalkyl group means an alkyl group in which a portion or all of hydrogen atoms have been substituted with fluorine, and a perfluoroalkoxy group means an alkoxy group in which a portion or all of hydrogen atoms have been substituted with fluorine.

Unless particularly stated otherwise herein, all compounds or substituents may be substituted or unsubstituted. Here, being "substituted" means that a hydrogen atom has been replaced with any one selected from the group consisting of a halogen atom, a hydroxyl group, a carboxyl group, a cyano group, a nitro group, an amino group, a thio group, a methylthio group, an alkoxy group, a nitrile group, an aldehyde group, an epoxy group, an ether group, an ester group, a carbonyl group, an acetal group, a ketone group, an alkyl group, a perfluoroalkyl group, a cycloalkyl group, a heterocycloalkyl group, an allyl group, a benzyl group, an aryl group, a heteroaryl group, derivatives thereof, and combinations thereof.

Unless particularly stated otherwise herein, the prefix hetero- means that a carbon atom is substituted with one to three heteroatoms selected from the group consisting of N, O, S, P and CO.

Unless particularly stated otherwise herein, an alkyl group includes a linear or branched alkyl group having 1 to 10 carbon atoms, an alkanediyl means an alkanediyl having 1 to 10 carbon atoms, an alkenediyl means an alkenediyl having 2 to 10 carbon atoms, and an alkoxy group means an alkoxy group having 1 to 10 carbon atoms. A perfluoroalkyl group means a perfluoroalkyl group having 1 to 10 carbon atoms, a perfluoroalkoxy group means a perfluoroalkoxy group having 1 to 10 carbon atoms, a cycloalkyl group means a cycloalkyl group having 3 to 32 carbon atoms, and a heterocycloalkyl group means a heterocycloalkyl group having 2 to 32 carbon atoms. An aryl group means an aryl group having 6 to 30 carbon atoms, and a heteroaryl group means a heteroaryl group having 2 to 30 carbon atoms.

Hereinafter, the present invention will be described in more detail.

The photoacid generator is represented by the following formula (1):

[Chemical Formula 1]

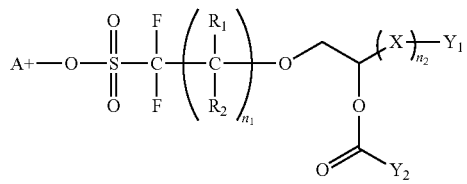

In the formula (1), $R_1$ and $R_2$ each independently represent any one selected from the group consisting of a hydrogen atom, an alkyl group, an alkoxy group, a perfluoroalkyl group, a perfluoroalkoxy group, a halogen atom, a hydroxyl group, a carboxyl group, a cyano group, a nitro group, an amino group and a thio group, and may be preferably a hydrogen atom or an alkyl group.

$n_1$ represents an integer of 1 or 2, and $n_2$ represents a integer from 0 to 5, and may be preferably an integer from 0 to 3.

X represents any one selected from the group consisting of an alkanediyl, an alkenediyl, NR', S, O, CO and combinations thereof, and R' represents any one selected from the group consisting of a hydrogen atom and an alkyl group.

Specifically, X may be any one selected from the group consisting of —O—, —OCH$_2$—, —OCH(Cl)—, —CO—, —COCH$_2$—, —COCH$_2$CH$_2$—, —CH$_2$—, —CH$_2$CH$_2$—, —CH$_2$—O—, —CH$_2$—O—CH$_2$—, —CH$_2$CH$_2$—, —CH$_2$—O—CH$_2$CH$_2$—, —CH$_2$CH$_2$—O—CH$_2$—, —CH$_2$CH$_2$CH$_2$—O—, —CH$_2$—O—CH$_2$CH$_2$CH$_2$—, —CH$_2$CH$_2$—O—CH$_2$CH$_2$—, —CH$_2$CH$_2$CH$_2$—O—CH$_2$—, —CH(CH$_3$)—, —C(CH$_3$)$_2$CH$_2$—, —CH(CH$_3$)CH$_2$—, —CH(CH$_2$CH$_3$)—, —CH(OCH$_3$)—, —C(CF$_3$)(OCH$_3$)—, —CH$_2$—S—, —CH$_2$—S—CH$_2$—, —CH$_2$CH$_2$—S—, —CH$_2$—S—CH$_2$CH$_2$—, —CH$_2$CH$_2$—S—CH$_2$—, —CH$_2$CH$_2$CH$_2$—S—, —CH$_2$—S—CH$_2$CH$_2$CH$_2$—, —CH$_2$CH$_2$—S—CH$_2$CH$_2$—, —CH$_2$CH$_2$CH$_2$—S—CH$_2$—, —CH(CH$_2$)CH—, —C(CH$_2$CH$_2$)—, —CH$_2$CO—, —CH$_2$CH$_2$CO—, —CH(CH$_3$)CH$_2$CO—, —CH(OH)—, —C(OH)(CH$_3$)—, —CH(F)—, —CH(Br)—, —CH(Br)CH(Br)—, —CH=CH—, —CH$_2$CH=CH—, —CH=CHCH$_2$—, —CH=CH—O—, —CH=CH—S— and —CH=CHCO—.

$Y_1$ and $Y_2$ may be each independently any one selected from the group consisting of an alkyl group, an alkenyl group, an alkoxy group, a cycloalkyl group, a heterocycloalkyl group, an aryl group, and a heteroaryl group. Specifically, $Y_1$ and $Y_2$ may be each independently any one selected from the group consisting of an alkyl group, an alkenyl group, an alkoxy group, a cyclopentyl group, a cyclohexyl group, a decahydronaphthalene group, an octahydro-1H-indene group, an adamantyl group, a norbornyl group, a tetrahydrofuran group, a polycyclic cycloalkyl group containing a norbornyl group having 10 to 30 carbon atoms, a phenyl group, a naphthyl group, a biphenyl group, an anthryl group, a phenanthrene group, a fluorenyl group, a pyrene group, a phenalene group, an indene group, a biphenylene group, a diphenylmethyl group, a tetrahydronaphthyl group, a dihydroanthryl group, a tetraphenylmethyl group and a triphenylmethyl group.

Among the carbon atoms of $Y_1$ or $Y_2$, one to three carbon atoms may be substituted with any one selected from the group consisting of —O—, —CO—, —S— and combinations thereof, and among the hydrogen atoms of $Y_1$ or $Y_2$, one to five hydrogen atoms may be substituted with any one selected from the group consisting of an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group, a cyano group, a nitro group, an amino group, a thio group, a methylthio group, a methoxy group, OR', COR', COOR', O and S. R' may be any one selected from the group consisting of an alkyl group and an aryl group.

More specifically, Y may be any one selected from the group consisting of an alkyl group, an alkenyl group, an alkoxy group, and groups represented by the following formulas (1-a) to (1-i) and formulas (2-a) to (2-l):

[Chemical Formula 1-a]

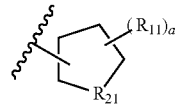

[Chemical Formula 1-b]

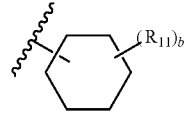

[Chemical Formula 1-c]

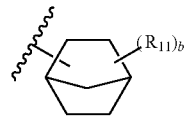

[Chemical Formula 1-d]

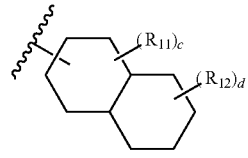

[Chemical Formula 1-e]

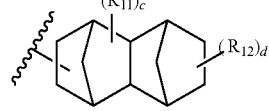

[Chemical Formula 1-f]

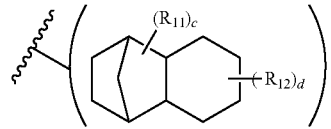

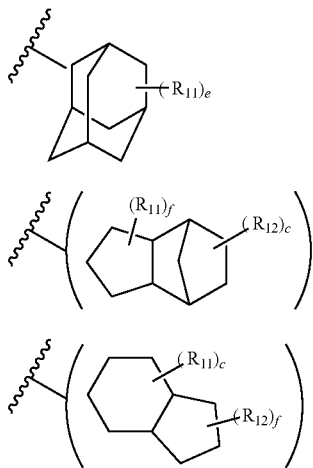

[Chemical Formula 1-g]

[Chemical Formula 1-h]

[Chemical Formula 1-i]

In the formulas (1-a) to (1-i), $R_{11}$ and $R_{12}$ each independently represent any one selected from the group consisting of a hydrogen atom, an alkyl group, an alkoxy group, a perfluoroalkyl group, a perfluoroalkoxy group, a halogen atom, a hydroxyl group, a carboxyl group, a cyano group, a nitro group, an amino group, a thio group, a methylthio group, a methoxy group, OR', COR', COOR', O and S, and R' represents any one selected from the group consisting of an alkyl group and an aryl group. When $R_{11}$ or $R_{12}$ is O or S, $R_{11}$ or $R_{12}$ represents a divalent substituent.

$R_{21}$ represents any one selected from the group consisting of $CR_{24}R_{25}$, O, CO, S and $NR_{23}$, and $R_{23}$ to $R_{25}$ each independently represent any one selected from the group consisting of a hydrogen atom, an alkyl group and an aryl group.

Furthermore, a, c and d each independently represent an integer from 0 to 9; b represents an integer from 0 to 11; e represents an integer from 0 to 15; f represents an integer from 0 to 7; and $0 \le c+d \le 17$, while $0 \le c+f \le 15$.

Specifically, in the formulas (1-a), (1-b), (1-d) and (1-g), $R_{11}$ may represent any one selected from the group consisting of a hydrogen atom, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group, a cyano group, a nitro group, an amino group, a thio group, a methylthio group, and a methoxy group.

Furthermore, in the formulas (1-c), (1-e), (1-f), (1-h) and (1-i), $R_{11}$ and $R_{12}$ may each independently represent any one selected from the group consisting of a hydrogen atom, an alkyl group having 1 to 6 carbon atoms, an alkoxy group having 1 to 6 carbon atoms, a perfluoroalkyl group having 1 to 4 carbon atoms, a perfluoroalkoxy group having 1 to 4 carbon atoms, a hydroxyalkyl group having 1 to 6 carbon atoms, a halogen atom, a hydroxyl group, a cyano group, a nitro group, an amino group, a thio group, a methylthio group, a methoxy group and combinations thereof.

[Chemical Formula 2-a]

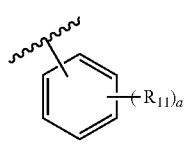

[Chemical Formula 2-b]

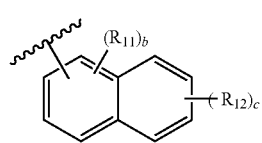

[Chemical Formula 2-c]

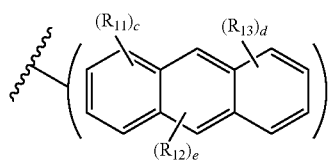

[Chemical Formula 2-d]

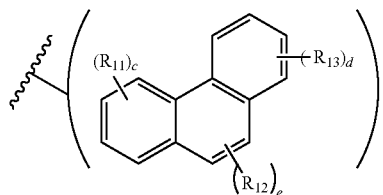

[Chemical Formula 2-e]

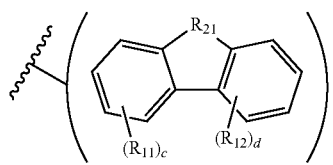

[Chemical Formula 2-f]

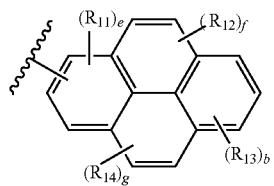

[Chemical Formula 2-g]

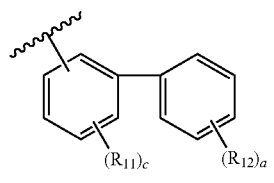

[Chemical Formula 2-h]

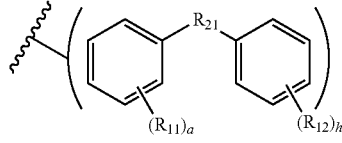

[Chemical Formula 2-i]

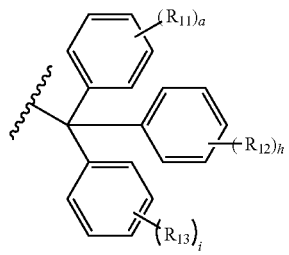

-continued

[Chemical Formula 2-j]

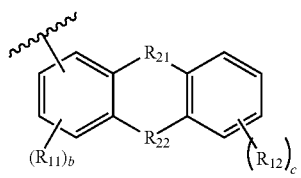

[Chemical Formula 2-k]

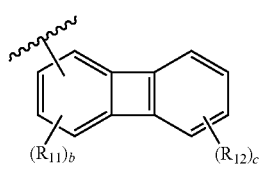

[Chemical Formula 2-l]

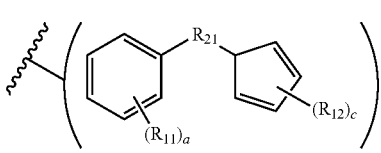

In the formulas (2-a) to (2-l), $R_{11}$, $R_{12}$, $R_{13}$ and $R_{14}$ each independently represent any one selected from the group consisting of an alkyl group, an alkoxy group, a perfluoroalkyl group, a perfluoroalkoxy group, a halogen atom, a hydroxyl group, a cyano group, a nitro group, an amino group, a thio group, a methylthio group, a methoxy group, OR', COR' and COOR', and R' represents any one selected from the group consisting of an alkyl group and an aryl group.

$R_{21}$ and $R_{22}$ each independently represent any one selected from the group consisting of $CR_{24}R_{25}$, O, CO, S and $NR_{23}$, and $R_{23}$ to $R_{25}$ each independently represent any one selected from the group consisting of a hydrogen atom, an alkyl group and an aryl group.

a, h and i each independently represent an integer from 0 to 5; b represents an integer from 0 to 3; c and d each independently represent an integer from 0 to 4; e, f and g each independently represent an integer from 0 to 2; and $0 \le c+d+e \le 9$.

Specifically, the photoacid generator may be any one selected from the group consisting of compounds represented by the following formulas (3-1) to (3-14):

[Chemical Formula 3-1]

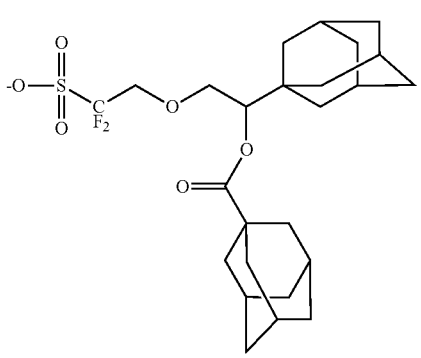

[Chemical Formula 3-2]

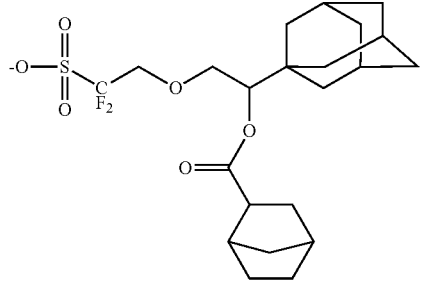

[Chemical Formula 3-3]

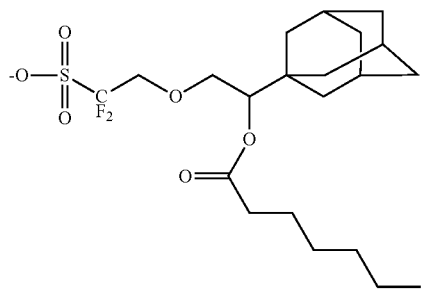

[Chemical Formula 3-4]

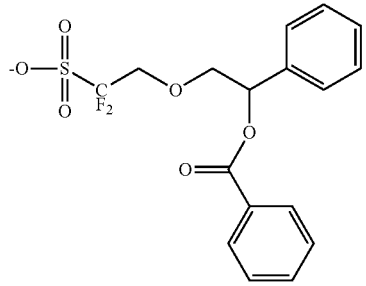

[Chemical Formula 3-5]

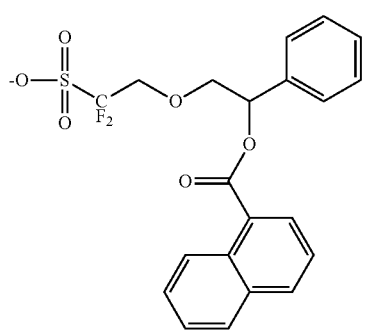

[Chemical Formula 3-6]

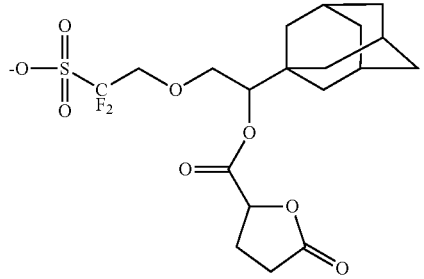

[Chemical Formula 3-7]

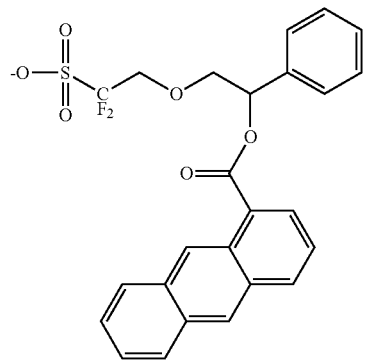

[Chemical Formula 3-8]

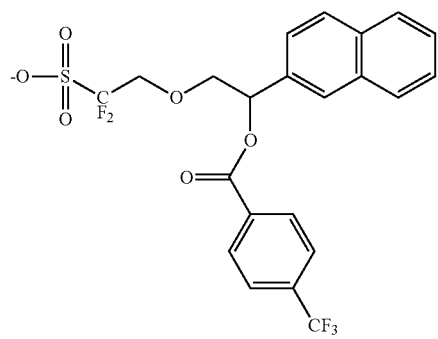

[Chemical Formula 3-9]

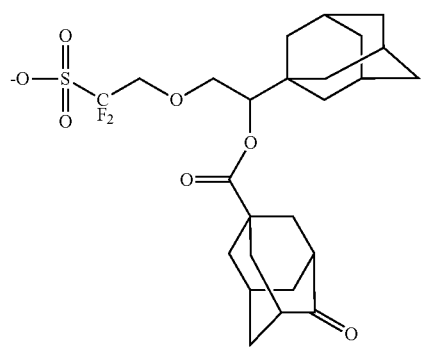

[Chemical Formula 3-10]

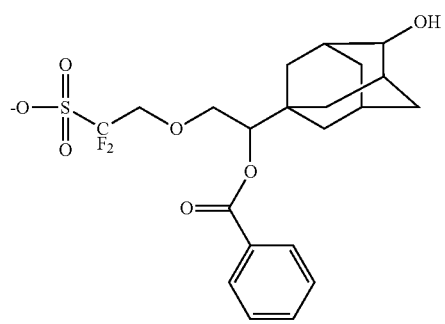

[Chemical Formula 3-11]

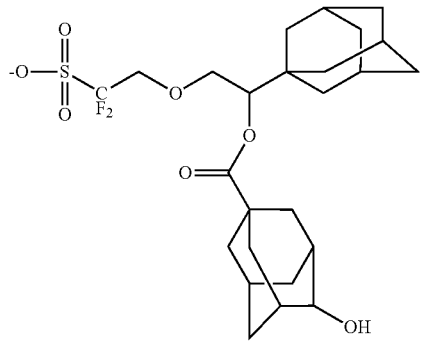

[Chemical Formula 3-12]

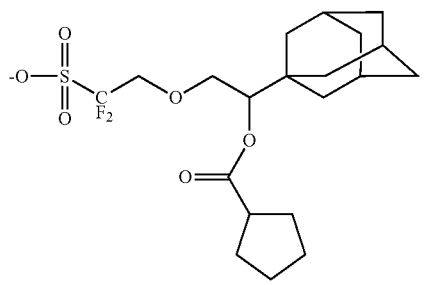

[Chemical Formula 3-13]

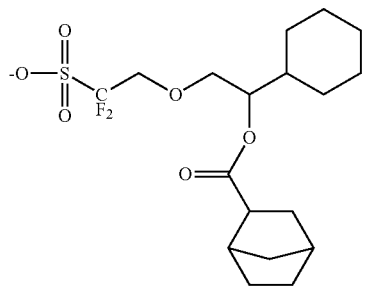

[Chemical Formula 3-14]

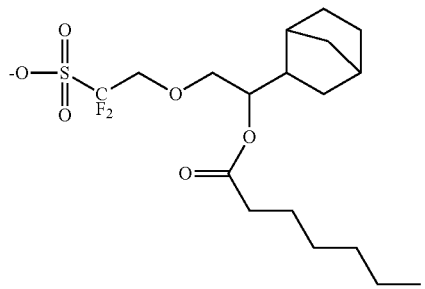

The photoacid generator is a compound represented by a sulfonic acid onium salt having an ester skeleton, and such a compound can also effective function as a photoacid generator for chemically amplified resist materials. Furthermore, the photoacid generator can maintain an appropriate contact angle at the time of ArF liquid immersion lithography, can reduce defects occurring during liquid immersion lithography, and has excellent solubility in resist solvents and excellent compatibility with resins.

Furthermore, the photoacid generator is a radiation-sensitive acid generator which responds to active radiation, particularly far-ultraviolet radiation or an electron beam, which are represented by KrF excimer laser light, ArF excimer laser light, or extreme ultraviolet (EUV) radiation. The photoacid generator exhibits satisfactory combustibility, has no problem of accumulation in human body, and has sufficiently high acidity of the acid generated (light-generated acid). The acid generated has an appropriate boiling point, and also has an appropriate short length of diffusion in the resist film. Furthermore, the photoacid generator has excellent solubility in resist solvents and excellent compatibility with resins, and can be easily produced by inexpensive methods.

In the formula (1), $A^+$ is an organic counterion, and its type is not particularly limited in the present invention. However, an example of an ion that can be used as the organic counterion may be any one selected from the group consisting of ions represented by the following formulas (4a) and (4b):

[Chemical Formula 4a]

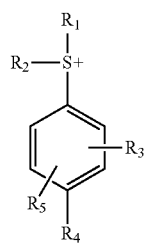

[Chemical Formula 4b]

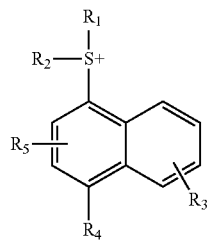

In the formulas (4a) and (4b), $R_1$ and $R_2$ each independently represent any one selected from the group consisting of a hydrogen atom, an alkyl group, an allyl group, a perfluoroalkyl group, an aryl group and combinations thereof; $R_1$ and $R_2$ can also be joined to form a saturated or unsaturated hydrocarbon ring having 3 to 30 carbon atoms.

$R_4$ represents any one selected from the group consisting of a halogen atom, an alkyl group, an alkoxy group, an aryl group, a thioalkoxy group, alkoxycarbonylmethoxy group, a thiophenoxy group, and combinations thereof.

$R_3$ and $R_5$ each independently represent any one selected from the group consisting of a hydrogen atom, an alkyl group, an allyl group, a perfluoroalkyl group, an aryl group and combinations thereof.

In the formulas (4a) and (4b), examples of the alkyl group include a methyl group, an ethyl group, a propyl group, an isopropyl group, an n-butyl group, a phenyl group, a hexyl group, and an octyl group, and examples of the alkoxy group include a methoxy group, an ethoxy group, a propoxy group, a butoxy group, a hexyloxy group, and an octyloxy group.

The organic counterion represented by the formula (4a) or (4b) may be any one selected from the group consisting of ions represented by the following formulas (4-i) to (4-xx):

[Chemical Formula 4-i]

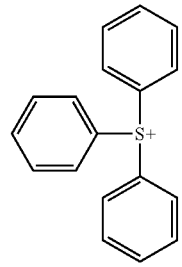

[Chemical Formula 4-ii]

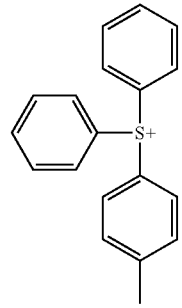

[Chemical Formula 4-iii]

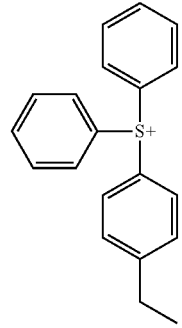

[Chemical Formula 4-iv]

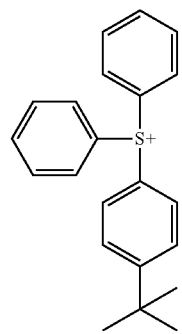

[Chemical Formula 4-v]

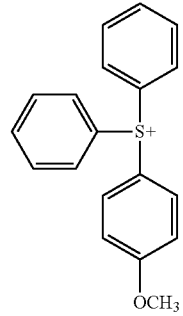

[Chemical Formula 4-vi]
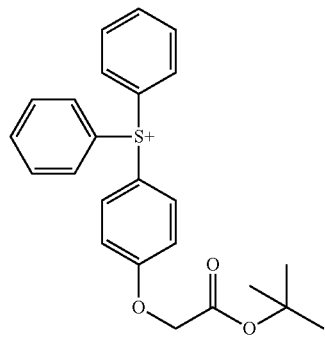
[Chemical Formula 4-vii]
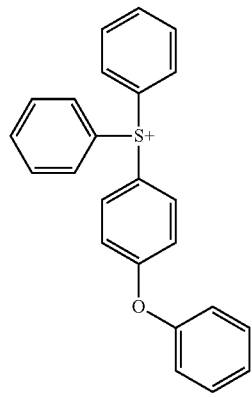
[Chemical Formula 4-viii]
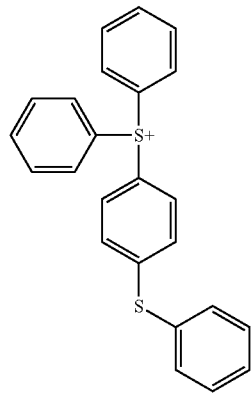
[Chemical Formula 4-ix]
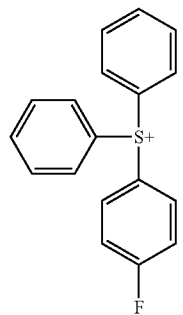
[Chemical Formula 4-x]
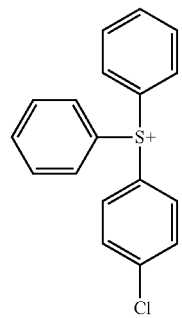
[Chemical Formula 4-xi]
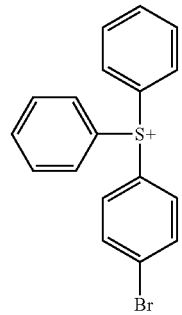
[Chemical Formula 4-xii]
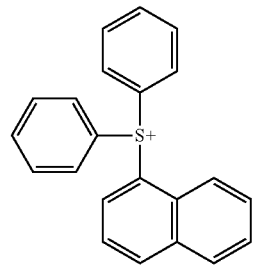
[Chemical Formula 4-xiii]

[Chemical Formula 4-xiv]

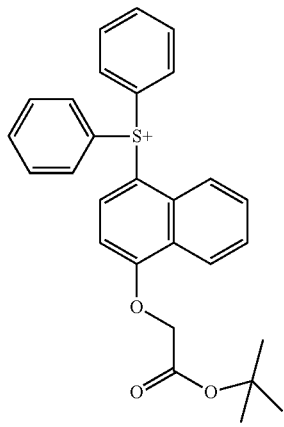

[Chemical Formula 4-xv]

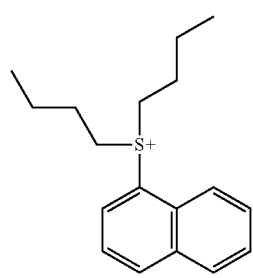

[Chemical Formula 4-xvi]

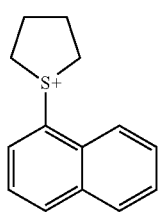

[Chemical Formula 4-xvii]

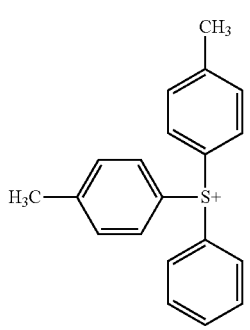

[Chemical Formula 4-xviii]

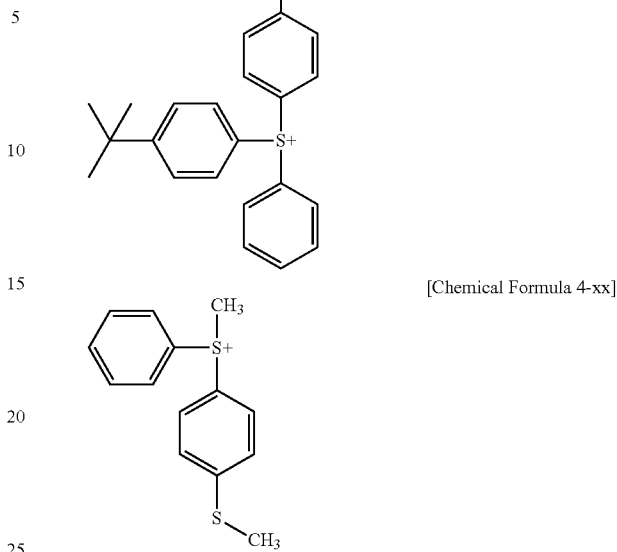

[Chemical Formula 4-xix]

[Chemical Formula 4-xx]

Furthermore, as the organic counterion, an one selected from the group consisting of ions represented by the following formulas (5a) and (5b):

[Chemical Formula 5a]

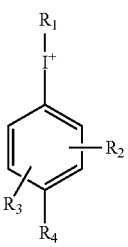

[Chemical Formula 5b]

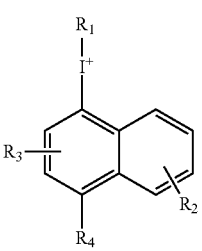

In the formulas (5a) and (5b), $R_1$ represents any one selected from the group consisting of a hydrogen atom, an alkyl group, an allyl group, a perfluoroalkyl group, an aryl group and combinations thereof.

$R_2$ and $R_3$ each independently represent any one selected from the group consisting of a hydrogen atom, an alkyl group, an allyl group, a perfluoroalkyl group, an aryl group and combinations thereof.

$R_4$ represents any one selected from the group consisting of a halogen atom, an alkyl group, an alkoxy group, an aryl group, a thioalkoxy group, an alkoxycarbonylmethoxy group, a thiophenoxy group and combinations thereof.

In the formulas (5a) and (5b), examples of the alkyl group include a methyl group, an ethyl group, a propyl group, an isopropyl group, an n-butyl group, a phenyl group, a hexyl group, and an octyl group; and examples of the alkoxy group include a methoxy group, an ethoxy group, a propoxy group, a butoxy group, a hexyloxy group, and an octyloxy group.

Furthermore, the organic counterion represented by the formula (5a) or (5b) may be any one selected from the group consisting of compounds represented by the following formula (5-i) to (5-ix):

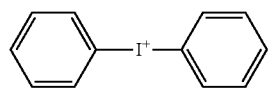

[Chemical Formula 5-i]

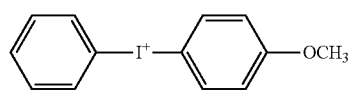

[Chemical Formula 5-ii]

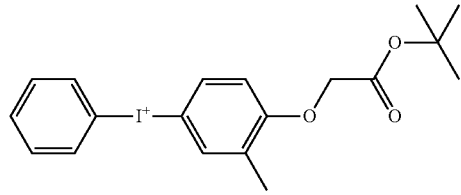

[Chemical Formula 5-iii]

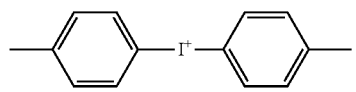

[Chemical Formula 5-iv]

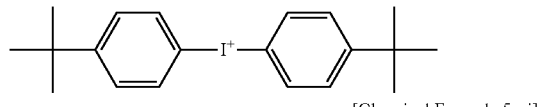

[Chemical Formula 5-v]

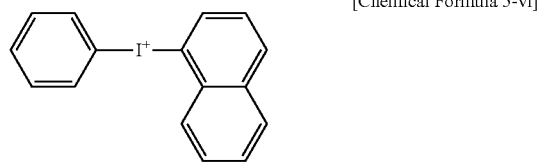

[Chemical Formula 5-vi]

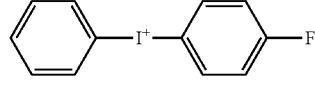

[Chemical Formula 5-vii]

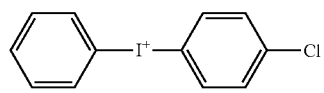

[Chemical Formula 5-viii]

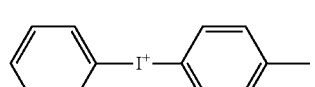

[Chemical Formula 5-ix]

The method for producing a photoacid generator includes a first step of allowing a hydroxysulfonic acid salt to react with oxirane and producing a hydroxyethoxysulfonic acid salt; a second step of allowing the hydroxyethoxysulfonic acid produced above to react with a carbonyl halide and thereby producing an intermediate; and a third step of subjecting the intermediate thus produced to a substitution reaction of the cation, and thereby producing a compound represented by the following formula (1).

In the first step, the hydroxysulfonic acid salt is allowed to react with oxirane, and thus a hydroxyethoxysulfonic acid salt is produced. The hydroxysulfonic acid salt may be represented by the following formula (6), the oxirane may be represented by the following formula (7), and the hydroxyethoxysulfonic acid salt may be represented by the following formula (8):

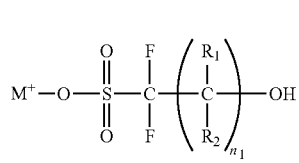

[Chemical Formula 6]

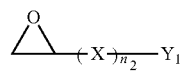

[Chemical Formula 7]

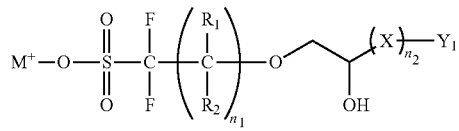

[Chemical Formula 8]

In the formulas (6) to (8), $Y_1$, X, $R_1$, $R_2$, $n_1$ and $n_2$ have the same meanings as defined for $Y_1$, X, $R_1$, $R_2$, $n_1$ and $n_2$ in the formula (1), and therefore, specific descriptions thereof will not be repeated here.

However, M+ in the formulas (6) to (8) represents an alkali metal ion, and specific examples include Li+, K+, and Na+, while Na+ is preferred.

The oxirane and the hydroxysulfonic acid salt may be allowed to react at a weight ratio of 1:1 to 1:3, and may be allowed to react at a weight ratio of 1:1.1 to 1:1.5. When the oxirane and the hydroxysulfonic acid salt are allowed to react at the weight ratio described above, the two compounds can be all consumed, and the efficiency of the reaction can be increased.

In the first step, the hydroxysulfonic acid salt and oxirane can be allowed to react in the presence of any one catalyst selected from the group consisting of an acidic catalyst and a basic catalyst. As the acidic catalyst, any one selected from the group consisting of sulfuric acid, hydrochloric acid, phosphoric acid, nitric acid, Lewis acid (BF3, AlCl3, FeCl3 or the like), and combinations thereof can be used, and as the basic catalyst, any one selected from the group consisting of NaH, KH, NaOMe, KOBut (potassium tert-butoxide), organic bases (Et3N (triethylamine), DIPEA (N,N-diisopropylethylamine), DBU (1,8-Diazabicyclo[5.4.0]undec-7-ene), and the like), and combinations thereof can be used. When a catalyst is used in the first step reaction, the desired product can be obtained in the minimum reaction time, and thus, the yield of the reaction can be increased.

Furthermore, the hydroxysulfonic acid salt and the carbonyl halide, and the catalyst can be allowed to react at a molar ratio of 1:0.05 to 1:2, and preferably can be allowed to react at a molar ratio of 1:0.1 to 1:1. The hydroxysulfonic acid salt and oxirane and the catalyst are allowed to react at the molar ratio described above, the reaction time can be accelerated, and the removal of residual catalyst may be achieved out more easily.

The reaction of the first step may be carried out in a solvent, and as the solvent, any one selected from the group consisting of esters, ethers, lactones, ketones, amides, alcohols, and combinations thereof can be used. Preferably, the solvent may be any one selected from the group consisting of dichloromethane, chloroform, dichloroethane, acetonitrile, toluene, methyl acetate, ethyl acetate, and combinations thereof.

Specifically, the reaction of the first step may include a process of dissolving the hydroxysulfonic acid salt and oxirane in a solvent, introducing the catalyst, and then allowing the mixture to react under stirring.

The stirring may be carried out at a temperature of 0° C. to 100° C. for 1 to 48 hours, and may be carried out at a temperature of 0° C. to 40° C. for 1 to 12 hours. When the process of stirring is achieved in the temperature and time ranges described above, the yield of the product can be increased, and the formation of side products may be minimized.

After completion of the reaction, the solvent is removed from the reaction liquid, the residue is made into a slurry in ethyl ether, the slurry is filtered, and then the filter cake is washed using ethyl ether and vacuum dried. Thus, the hydroxyethoxysulfonic acid salt can be produced.

In the second step, the hydroxyethoxysulfonic acid salt thus produced is allowed to react with a carbonyl halide, and thus an intermediate is produced. The carbonyl halide may be represented by the following formula (9), and the intermediate may be represented by the following formula (10).

[Chemical Formula 9]

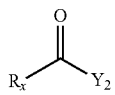

[Chemical Formula 10]

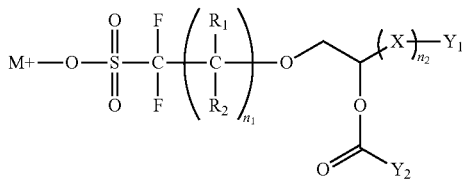

wherein in the formulas (9) and (10), $Y_1$, $Y_2$, X, $R_1$, $R_2$, $R_x$, $n_1$, $n_2$ and $M^+$ have the same meanings as defined for $Y_1$, $Y_2$, X, $R_1$, $R_2$, $R_x$, $n_1$, $n_2$ and $M^+$ in the formula (1) or (8), and therefore, specific descriptions thereof will not be repeated here.

The carbonyl halide and the hydroxyethoxysulfonic acid salt can be made to react at a weight ratio of 1:1 to 1:3, and preferably can be made to react at a weight ratio of 1:1.1 to 1:1.5. When the carbonyl halide and the hydroxyethoxysulfonic acid salt are allowed to react, both the two compounds can be consumed, and therefore, the reaction efficiency can be increased.

In the second step, the hydroxyethoxysulfonic acid salt and the carbonyl halide can be made to react in the presence of any one catalyst selected from the group consisting of an acidic catalyst and a basic catalyst. As the acidic catalyst, any one selected from the group consisting of sulfuric acid, hydrochloric acid, phosphoric acid, nitric acid, a Lewis acid ($BF_3$, $AlCl_3$, $FeCl_3$ or the like) and combinations thereof can be used, and as the basic catalyst, any one selected from the group consisting of NaH, Kit, NaOMe, potassium tert-butoxide (KOBut), an organic base (triethylamine ($Et_3N$), N,N-diisopropylethylamine (DIPEA), 1,8-diazabicyclo[5.4.0]undec-7-ene (DBU) or the like) and combinations thereof can be used. When the above-described catalysts are used in the second step reaction, a desired product can be acquired in a minimal reaction time, and therefore, the reaction yield can be increased.

Furthermore, the hydroxyethoxysulfonic acid salt and the carbonyl halide, and the catalyst can be made to react at a molar ratio of 1:0.05 to 1:10, and preferably at a molar ratio of 1:0.1 to 1:5. When the hydroxyethoxysulfonic acid salt, the carbonyl halide and the catalyst are made to react at the molar ratio described above, the reaction time can be shortened, and it can be made easier to remove any residual acidic catalyst.

The reaction of the second step can be carried out in the presence of a solvent, and any one selected from the group consisting of esters, ethers, lactones, ketones, amides, alcohols and combinations thereof can be used as the solvent. Preferably, the solvent may be any one selected from the group consisting of dichloromethane, chloroform, dichloroethane, acetonitrile, toluene, methyl acetate, ethyl acetate and combinations thereof.

Specifically, the reaction of the second step may include a process of dissolving the hydroxyethoxysulfonic acid salt and the carbonyl halide in a solvent, introducing a catalyst, and then allowing the mixture to react at a temperature of 20° C. to 100° C. for 1 to 12 hours, and preferably at a temperature of 40° C. to 80° C. for 1 to 6 hours. When the process is carried out under stirring at the temperature and time in the ranges described above, the yield of the product can be increased, and the production of side products can be minimized.

After completion of the reaction, the solvent is removed from the reaction liquid, the residue is made into a slurry with ethyl ether, and the slurry is filtered. Subsequently, the filter cake is washed using ethyl ether and dried in a vacuum.

In this manner, the intermediate can be produced.

In the third step, the intermediate thus produced is subjected to a substitution reaction of the cation, and thus a compound represented by the formula (1) is produced. The reaction for substituting the cation of the intermediate can be carried out by allowing the hydroxyethoxysulfonic acid salt to react with a compound represented by the following formula (11):

 [Chemical Formula 11]

wherein in the formula (11), $Z^-$ represents any one selected from the group consisting of $(OSO_2CF_3)^-$, $(OSO_2C_4F_9)^-$, $(OSO_2C_8F_{17})^-$, $(N(CF_3)_2)^-$, $(N(C_2F_5)_2)^-$, $(N(C_4F_9)_2)$, $(C(CF_3)_3)^-$, $(C(C_2F_5)_3)^-$, $(C(C_4F_9)_3)^-$, $F^-$, $Cl^-$, $Br^-$, $I^-$, $BF_4^-$, $AsF_6^-$ and $PF_6^-$.

A+ is an organic counterion, and since the definition of the organic counterion is the same as described in connection with the formula (1), specific description thereof will not be repeated here.

The intermediate and the compound represented by the formula (11) can be used at a molar ratio of 1:1 to 4:1, and preferably at a molar ratio of 1:1 to 2:1. When the compounds are used at the molar ratio described above, the reaction treatment time can be minimized, and side reactions caused by excessive use of the reactants can be suppressed.

The substitution reaction can be carried out using a recrystallization method, or a method of using a mixture of a solvent which well dissolves an obtained salt (good solvent) and a solvent which dissolves the salt poorly, to solidify the reaction product, and collecting the reaction product. A method of extracting the reaction product with a solvent, or a method of concentrating and collecting the reaction product can also be used.

Preferably, the substitution reaction can be carried out by dissolving the reactants in dichloromethane and water to form two layers, and then allowing the substitution to occur by stirring, and when such a two-layer reaction method is used, it is advantageous in that any additional methods for the separation of the product are not required. The stirring may be carried out in 2 to 6 hours, and may also be carried out in 2 to 4 hours. When the reaction is carried out in the time range described above, there is an effect that the yield of the product can be increased to the maximum.

When the compound represented by the formula (1) is produced through the production method described above, the compound represented by the formula (1) can be produced by a simple method, and the compound can be produced using an epoxy compound, which is industrially easily available.

The resist composition according to another embodiment of the present invention includes a photoacid generator represented by the formula (1). The resist composition depends on the conventional constitution of resist compositions, and therefore, specific description thereof will not be repeated here.

The photoacid generator of the present invention can maintain an appropriate contact angle at the time of ArF liquid immersion lithography, can reduce detects occurring during liquid immersion lithography, and has excellent solubility in resist solvents and excellent compatibility with resins. Furthermore, the photoacid generator can be produced by an efficient and simple method using an epoxy compound, which is industrially easily available.

EXAMPLES

Hereinafter, the present invention will be described in detail by way of Examples, so that a person having ordinary skill in the art to which the present invention is pertained can easily carry out the invention. However, the present invention may be realized in various different forms, and is not intended to be limited to the Examples described herein.

Synthesis of Photoacid Generator

Synthesis Example 1

Step 1

As shown in the following reaction scheme (1-1), 20 g of 1,1-difluoro-2-hydroxyethanesulfonic acid sodium salt and 19.4 g of 2-adamantan-1-yloxirane were dissolved in 300 ml of dichloroethane, and the solution was stirred at normal temperature. 1 ml of sulfuric acid was slowly added dropwise to the mixture at normal temperature, and then the mixture was stirred for 2 hours.

After completion of the reaction, the reaction solvent was removed, and the residue was prepared into a slurry in ethyl ether and was filtered. After filtering, the filter cake was washed with distilled water and ethyl ether, and was vacuum dried. Thus, 33.5 g (yield 85%) of 2-(2-adamantan-1-yl-2-hydroxyethoxy)-1,1-difluoroethanesulfonic acid sodium salt was obtained, and its structure was confirmed by $^1$H-NMR.

$^1$H-NMR (dimethyl sulfoxide-d6, tetramethylsilane): δ(ppm) 1.11-1.64 (m, 15H), 3.49-3.55 (m, 3H), 4.25 (t, 2H)

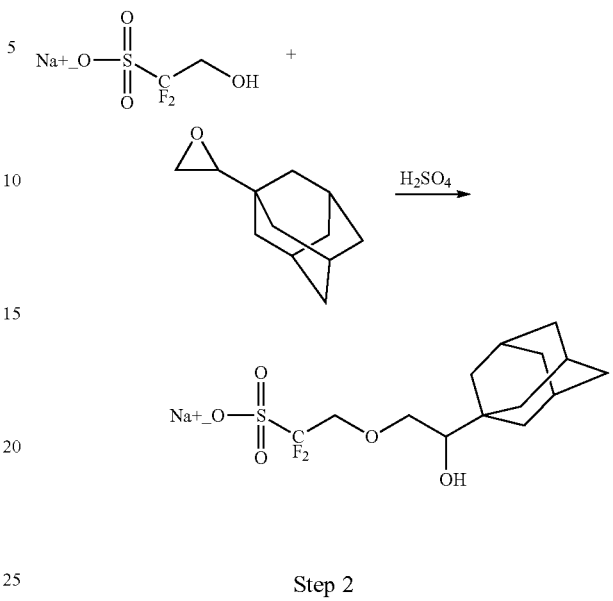

[Reaction Scheme 1-1]

Step 2

As shown in the following reaction scheme (1-2), 20 g of the 2-(2-adamantan-1-yl-2-hydroxyethoxy)-1,1-difluoroethanesulfonic acid sodium salt produced in the Step 1, and 13.2 g of adamantanecarbonyl chloride were dissolved in 300 ml of dichloroethane and the solution was stirred at normal temperature. 12 ml of triethylamine was slowly added dropwise thereto at normal temperature, and then the reaction temperature was raised to 60° C. At that temperature, the mixture was heated and stirred for 2 hours.

After completion of the reaction, the reaction solvent was removed, and the residue was made into a slurry with ethyl ether and filtered. After the filtration, the filter cake was washed with distilled water and ethyl ether, and was dried in a vacuum. The structure of the product was confirmed by $^1$H-NMR, and thus 33.2 g (yield 87%) of adamantane-1-carboxylic acid 1-adamantan-1-yl-2-(2,2-difluoro-2-sulfoethoxy)ethyl ester sodium salt having the following structural formula was obtained.

$^1$H-NMR (dimethyl sulfoxide-d$_6$, tetramethylsilane): δ(ppm) 1.11-1.64 (m, 30H), 3.62 (d, 2H), 4.25 (m, 3H)

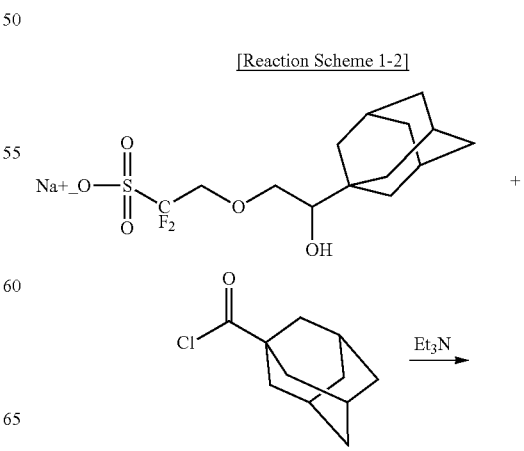

[Reaction Scheme 1-2]

-continued

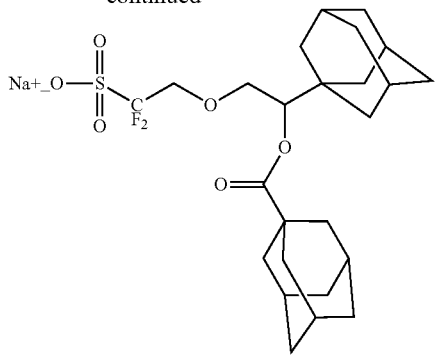

Step 3

As shown in the following reaction scheme 1-3, the adamantane-1-carboxylic acid 1-adamantan-1-yl-2-(2,2-difluoro-2-sulfoethoxy)ethyl ester sodium salt produced in the Step 2 and diphenyl methylphenyl sulfonium trifluoromethanesulfonate were allowed to react. Thus, adamantane-1-carboxylic acid 1-adamantan-1-yl-2-(2,2-difluoro-2-sulfoethoxy)ethyl ester diphenylfluorophenylsulfonium salt was obtained, and its structure was confirmed by $^1$H-NMR.

$^1$H-NMR (chloroform-d$_3$, tetramethylsilane): δ(ppm) 1.11-1.64 (m, 30H), 3.62 (d, 2H), 4.25 (m, 3H), 7.48 (d, 2H), 7.65-7.76 (m, 12H)

[Reaction Scheme 1-3]

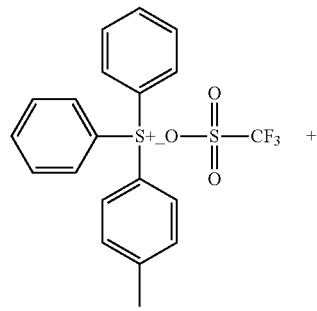

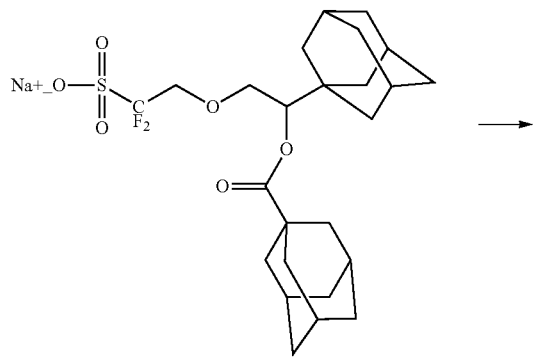

-continued

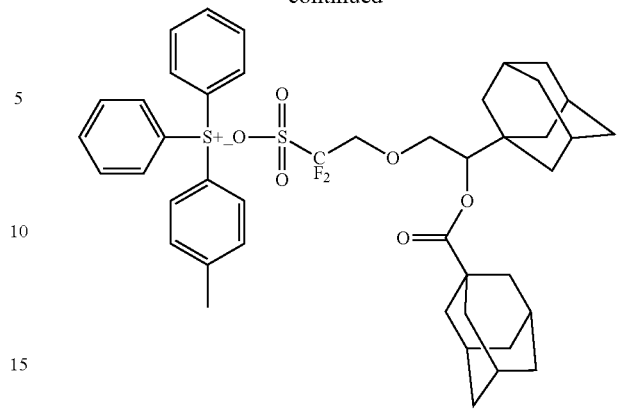

Synthesis Example 2

Step 1

The process of the Step 1 of Synthesis Example 1 was carried out in the same manner, and thus 2-(2-adamantan-1-yl-2-hydroxyethoxy)-1,1-difluoroethanesulfonic acid sodium salt was obtained.

Step 2

As shown in the following reaction scheme 2-2, 20 g of 2-(2-adamantan-1-yl-2-hydroxyethoxy)-1,1-difluoroethanesulfonic acid sodium salt produced in the Step 1, and 10.5 g of bicyclo[2.2.1]heptane-2-carbonyl chloride were dissolved in 300 ml of dichloroethane, and the solution was stirred at normal temperature. 8.4 g of triethylamine was slowly added dropwise thereto at normal temperature, and then the reaction temperature was raised to 60° C. At that temperature, the mixture was heated and stirred for 2 hours.

After completion of the reaction, the reaction solvent was removed, and the residue was made into a slurry with ethyl ether and filtered. After the filtration, the filter cake was washed with distilled water and ethyl ether, and was dried in a vacuum. The structure of the product was confirmed by $^1$H-NMR, and thus 24 g (yield 90%) of bicyclo[2.2.1]heptane-2-carboxylic acid 1-adamantan-1-yl-2-(2,2-difluoro-2-sulfoethoxy)ethyl ester sodium salt was obtained.

$^1$H-NMR (dimethyl sulfoxide-d$_6$, tetramethylsilane): δ(ppm) 1.11-1.58 (m, 22H), 1.83 (m, 2H), 2.13 (m, 1H), 2.33 (m, 1H), 3.62 (d, 2H), 4.25 (m, 3H)

[Reaction Scheme 2-2]

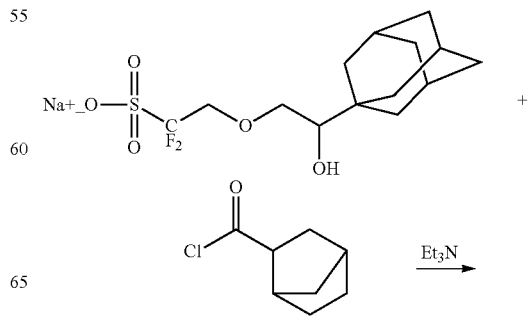

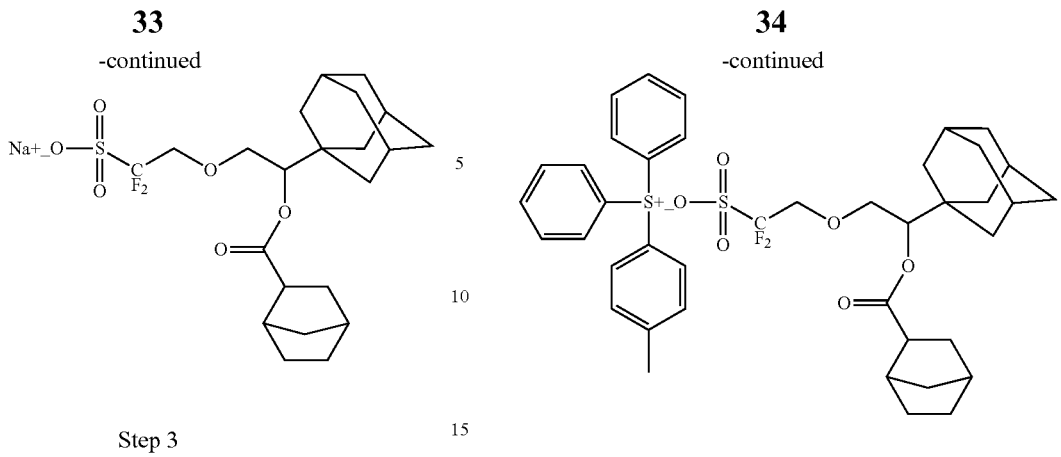

Step 3

As shown in the following reaction scheme 2-3, the bicyclo[2.2.1]heptane-2-carboxylic acid 1-adamantan-1-yl-2-(2,2-difluoro-2-sulfoethoxy)ethyl ester sodium salt produced in the Step 2 and diphenyl methylphenyl sulfonium trifluoromethanesulfonate were allowed to react with each other, and thus bicyclo[2.2.1]heptane-2-carboxylic acid 1-adamantan-1-yl-2-(2,2-difluoro-2-sulfoethoxy)ethyl ester diphenyl fluorophenyl sulfonium salt was obtained. Its structure was confirmed by $^1$H-NMR.

$^1$H-NMR (chloroform-d3, tetramethylsilane): δ(ppm) 1.09-1.56 (m, 22H), 1.81 (m, 2H), 2.14 (m, 1H), 2.32 (m, 1H), 3.61 (d, 2H), 4.27 (m, 3H) 7.48 (d, 2H), 7.65-7.76 (m, 12H)

[Reaction Scheme 2-3]

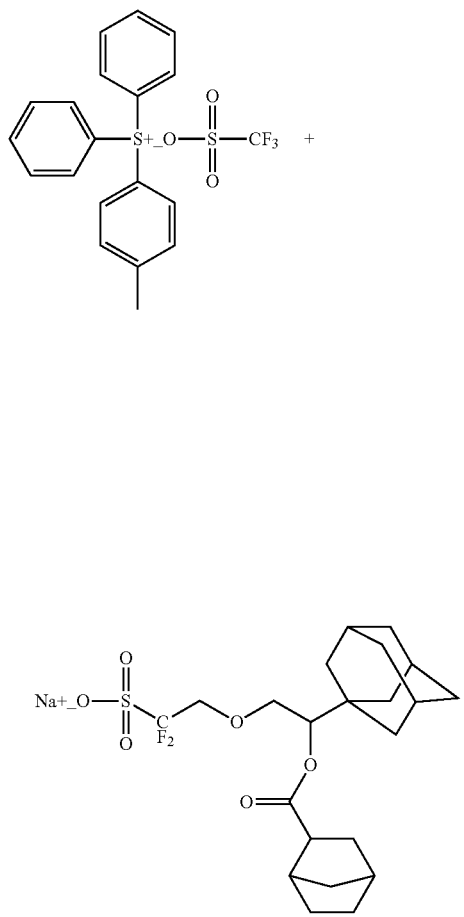

Synthesis Example 3

Step 1

As shown in the following reaction scheme (3-1), 20 g of 1,1-difluoro-2-hydroxyethanesulfonic acid sodium salt and 13 g of 2-phenyloxirane were dissolved in 300 ml of dichloroethane, and the solution was stirred at normal temperature. 1 ml of sulfuric acid was slowly added dropwise thereto at normal temperature, and then the mixture was stirred for 2 hours.

After completion of the reaction, the reaction solvent was removed, and the residue was made into a: slurry with ethyl ether and filtered. After the filtration, the filter cake was washed with distilled water and ethyl ether, and was dried in a vacuum. The structure of the product was confirmed by $^1$H-NMR, and thus 28.4 g (yield 86%) of 1,1-difluoro-2-(2-hydroxy-2-phenylethoxy)ethanesulfonic acid sodium salt having the following structural formula was obtained.

$^1$H-NMR (dimethyl sulfoxide-d6, tetramethylsilane): δ(ppm) 3.86 (dd, 2H), 4.26 (t, 2H), 4.85 (t, 1H), 7.18-7.23 (m, 5H)

[Reaction Scheme 3-1]

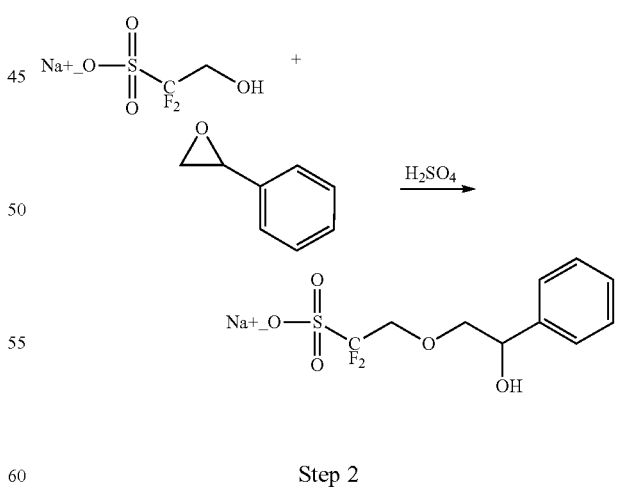

Step 2

As shown in the following reaction scheme (3-2), 20 g of the 1,1-difluoro-2-(2-hydroxy-2-phenylethoxy)ethanesulfonic acid sodium salt produced in the Step 1 and 11 g of benzoyl chloride were dissolved in 300 ml of dichloroethane, and the solution was stirred at normal temperature. 11 ml of triethylamine was slowly added dropwise thereto at normal temperature, and then the reaction temperature was raised to 60° C. At that temperature, the mixture was heated and stirred for 2 hours.

After completion of the reaction, the reaction solvent was removed, and the residue was made into a slurry with ethyl ether and filtered. After the filtration, the filter cake was washed with distilled water and ethyl ether, and was dried in a vacuum. The structure of the product was confirmed by ¹H-NMR, and thus 29 g (yield 92%) of benzoic acid 2-(2,2-difluoro-2-sulfoethoxy)-1-phenylethyl ester sodium salt was obtained.

¹H-NMR (dimethyl sulfoxide-d₆, internal standard: tetramethylsilane): δ(ppm) 4.12 (m, 2H), 4.25 (t, 2H), 5.57 (m, 1H), 7.17-7.22 (m, 5H), 7.37-7.98 (m, 5H)

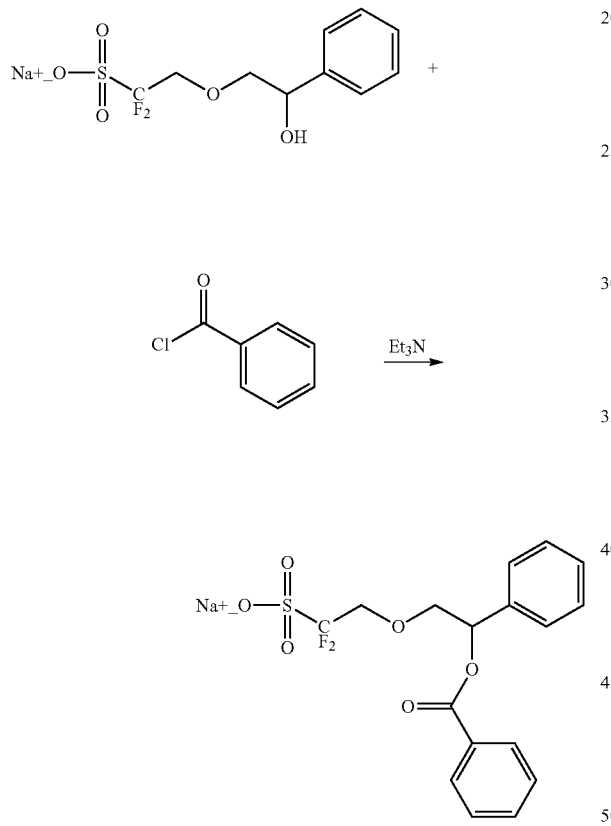

[Reaction Scheme 3-2]

Step 3

As shown in the following reaction scheme 3-3, the benzoic acid 2-(2,2-difluoro-2-sulfoethoxy)-1-phenylethyl ester sodium salt produced in the Step 2, and diphenyl methylphenyl sulfonium trifluoromethanesulfonate were allowed to react with each other, and thus benzoic acid 2-(2,2-difluoro-2-sulfoethoxy)-1-phenylethyl ester diphenyl fluorophenyl sulfonium salt was obtained. Its structure was confirmed by ¹H-NMR.

¹H-NMR (chloroform-d₃, tetramethylsilane): δ(ppm) 4.12 (m, 2H), 4.25 (t, 2H), 5.57 (m, 1H), 7.1.7-7.22 (m, 5H), 7.37-7.98 (m, 19H)

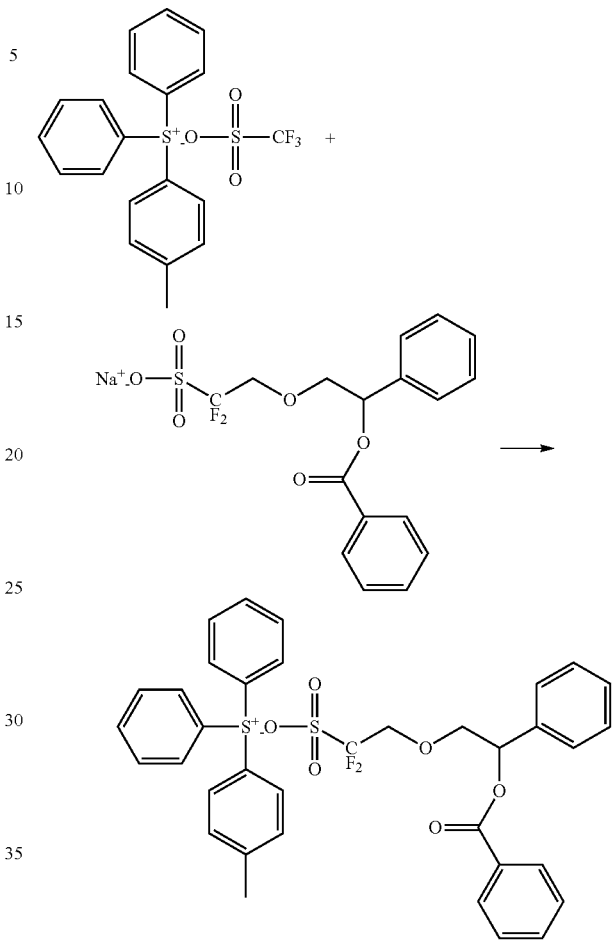

[Reaction Scheme 3-3]

Synthesis Example 4

Step 1

Synthesis was carried out in the same manner as in the Step 1 of Synthesis Example 3, and thus 1,1-difluoro-2-(2-hydroxy-2-phenylethoxy)ethanesulfonic acid sodium salt was obtained.

Step 2

As shown in the following reaction scheme (4-2), 20 g of the 1,1-difluoro-2-(2-hydroxy-2-phenylethoxy)ethanesulfonic acid sodium salt produced in the Step 1 and 15 g of 1-naphthalenecarbonyl chloride were dissolved in 300 ml of dichloroethane, and the solution was stirred at normal temperature. 12 ml of triethylamine was slowly added dropwise thereto at normal temperature, and then the reaction temperature was raised to 60° C. At that temperature, the mixture was heated and stirred for 2 hours.

After completion of the reaction, the reaction solvent was removed, and the residue was made into a slurry with ethyl ether and filtered. After the filtration, the filter cake was washed with distilled water and ethyl ether, and was dried in a vacuum. The structure of the product was confirmed by ¹H-NMR, and thus 25.3 g (yield 84%) of naphthalene-1- carboxylic acid 2-(2,2-difluoro-2-sulfoethoxy)-1-phenyl-ethyl ester sodium salt was obtained.

¹H-NMR (dimethyl sulfoxide-d₆, tetramethylsilane): δ(ppm) 4.13 (m, 2H), 4.25 (t, 2H), 5.58 (m, 1H), 7.17-7.21 (m, 5H), 7.37-7.52 (m, 4H), 7.89 (d, 1H), 8.12 (d, 1H), 8.97 (d, 1H)

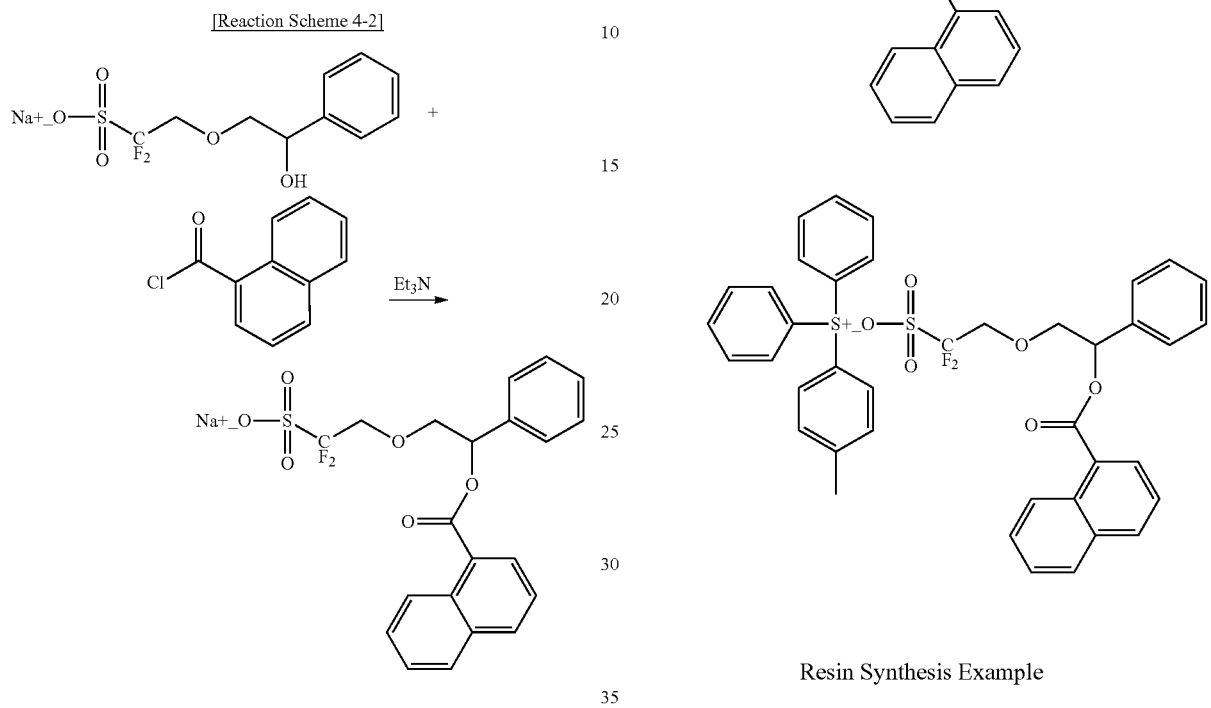

Step 3

As shown in the following reaction scheme 4-3, the naphthalene-1-carboxylic acid 2-(2,2-difluoro-2-sulfoethoxy)-1-phenylethyl ester sodium salt produced in the Step 2 and diphenyl methylphenyl sulfonium trifluoromethanesulfonate were allowed to react with each other, and thus naphthalene-1-carboxylic acid 2-(2,2-difluoro-2-sulfoethoxy)-1-phenylethyl ester diphenyl fluorophenyl sulfonium salt was obtained. Its structure was confirmed by ¹H-NMR.

¹H-NMR (chloroform-d₃, tetramethylsilane): δ(ppm) 4.12 (m, 2H), 4.25 (t, 2H), 5.57 (m, 1H), 7.17-7.21 (m, 5H), 7.37-7.77 (m, 18H), 7.89 (d, 1H), 8.12 (d, 1H), 8.97 (d, 1H)

[Reaction Scheme 4-3]

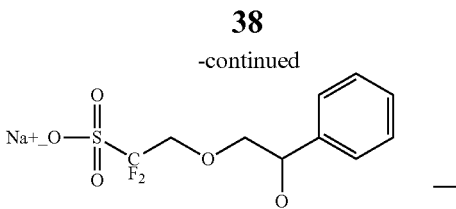

Resin Synthesis Example

3-Bicyclo[2.2.1]hept-5-en-2-yl-3-hydroxypropionic acid t-butyl ester (hereinafter, referred to as BHP), 1-methyladamantane acrylate, and γ-butyrolactonemethyl acrylate were introduced at a molar ratio of 1:1:1. 1,4-Dioxane was added as a polymerization solvent in an amount of 300 parts by weight relative to 100 parts by weight of the total amount of the reaction monomers, azobisisobutyronitrile was added as an initiator in an amount of 4 molar parts relative to 100 molar parts of the total reaction monomers, and the mixture was allowed to react for 16 hours at 65° C.

After the reaction, the reaction solution was precipitated with n-hexane, and the precipitate was removed and dried in a vacuum. Thus, a copolymer represented by the following formula (12) and having a weight average molecular weight of about 8,500 g/mol was obtained.

[Chemical Formula 12]

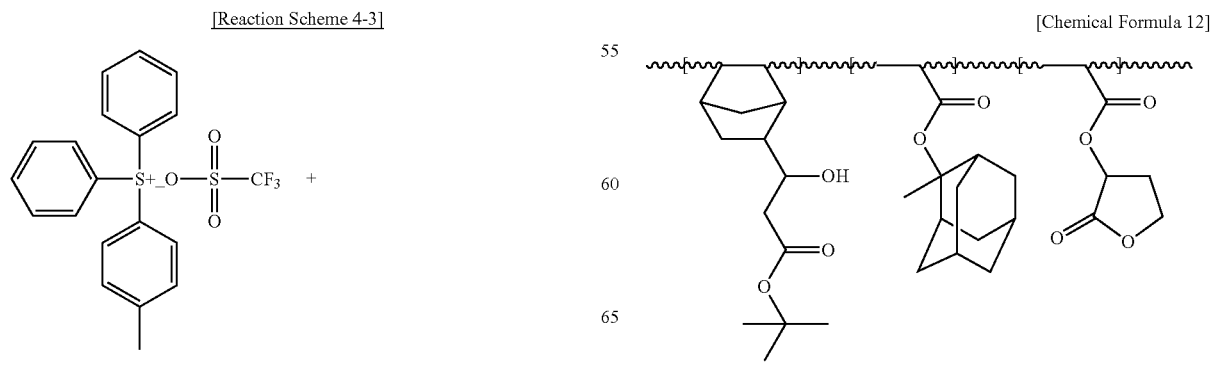

Experiment Examples

Example 1

100 Parts by weight of the resin obtained in the Resin Synthesis Example, 4 parts by weight of the adamantane-1-carboxylic acid 1-adamantan-1-yl-2-(2,2-difluoro-2-sulfoethoxy)ethyl ester diphenyl fluorophenyl sulfonium salt produced in Synthesis Example 1 as a photoacid generator, and 0.5 parts by weight of tetramethylammonium hydroxide as a basic additive were dissolved in 1,000 parts by weight of propylene glycol methyl ether acetate, and then the solution was filtered through a 0.2-μm membrane filter. Thus, a resist composition was prepared.

The resist composition thus obtained was applied on a substrate using a spinner, and was dried at 110° C. for 90 seconds to form a film having a thickness of 0.20 μm. The film thus formed was exposed using an ArF excimer laser stepper (lens aperture number: 0.78), and then the film was heat treated for 90 seconds at 110° C. Subsequently, the film was developed with a 2.38 wt % aqueous solution of tetramethylammonium hydroxide for 40 seconds, and was washed and dried. Thus, a resist pattern was formed.

Example 2

A resist composition was prepared in the same manner as in Example 1, except that the photoacid generator produced in Synthesis Example 2 was used in place of the photoacid generator that was produced in Synthesis Example 1 and used in Example 1. Thus, a resist pattern was formed.

Example 3

A resist composition was prepared in the same manner as in Example 1, except that the photoacid generator produced in Synthesis Example 4 was used in place of the photoacid generator that was produced in Synthesis Example 1 and used in Example 1. Thus, a resist pattern was formed.

Comparative Example

A resist composition was prepared in the same manner as in Example 1, except that triphenylsulfonium triflate was used in place of the photoacid generator that was produced in Synthesis Example 1 and used in Example 1. Thus, a resist pattern was formed.

Various evaluations were carried out for the resist patterns produced in Examples 1 to 3. The results are presented in the following Table 1.

In the following Table 1, the amount of exposure used to form a 0.10-μm line-and-space (L/S) pattern after development at a line width of 1:1 was designated as the optimum amount of exposure, and this optimum amount of exposure was designated as sensitivity. The minimum pattern dimension resolved at this time was designated as resolution.

Furthermore, in the case of line edge roughness (LER), the pattern roughness in the 0.10-μm line-and-space (L/S) pattern formed after development was observed, and the LER was measured (a smaller number indicates superior LER).

TABLE 1

|  | Resin (100 parts by weight) | PAG (parts by weight) | Base (parts by weight) | Sensitivity (mJ/cm$^2$) | Resolution (nm) | LER |
|---|---|---|---|---|---|---|
| Example 1 | Resin Synthesis Example | 4.0 | 0.5 | 14 | 70 | 3 |
| Example 2 | Resin Synthesis Example | 4.0 | 0.5 | 13 | 80 | 4 |
| Example 3 | Resin Synthesis Example | 4.0 | 0.5 | 12 | 80 | 5 |
| Comparative Example 1 | Resin Synthesis Example | 4.0 | 0.5 | 17 | 100 | 7 |

It was confirmed that the resist compositions prepared in Examples 1 to 3 have satisfactory developability with an aqueous solution of tetramethylammonium hydroxide, and satisfactory adhesiveness of the formed resist pattern to a substrate, as compared with the resist composition prepared in Comparative Example 1. It can be seen from the results of Table 1 that the resist compositions prepared in Examples 1 to 3 have superior sensitivity, resolution and LER characteristics as compared with the resist composition prepared in Comparative Example 1.

Preferred embodiments of the present invention have been described in detail in the above, but the scope of the invention is not limited to the specific details and representative embodiments shown and described herein. Accordingly, various modification's may be made without departing from the spirit or scope of the general inventive concept as defined by the appended claims and their equivalents.

What is claimed is:

1. A photoacid generator represented by the following formula (1):

[Chemical Formula 1]

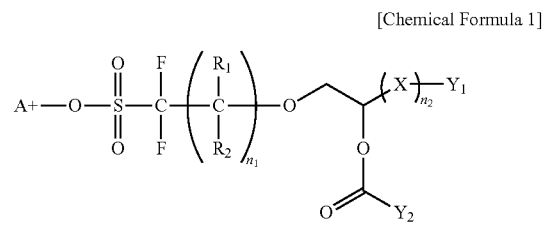

wherein in the formula (1), $Y_1$ and $Y_2$ each independently represent any one selected from the group consisting of a cycloalkyl group, a heterocycloalkyl group, an aryl group and a heteroaryl group;

X represents any one selected from the group consisting of an alkanediyl, an alkenediyl, NR', S, O, CO and combinations thereof, while R' represents any one selected from the group consisting of a hydrogen atom and an alkyl group;

$R_1$ and $R_2$ each independently represent any one selected from the group consisting of a hydrogen atom, an alkyl group, an alkoxy group, a perfluoroalkyl group, a perfluoroalkoxy group, a halogen group, a hydroxyl group, a carboxyl group, a cyano group, a nitro group, an amino group and a thio group;

$n_1$ represents an integer or 1 or 2;

$n_2$ represents an integer from 0 to 5; and $A^+$ represents an organic counterion.

2. The photoacid generator according to claim 1, wherein $Y_1$ and $Y_2$ each independently represent any one selected from the group consisting of a cyclopentyl group, a cyclohexyl group, a decahydronaphthalene group, an octahydro-1H-indene group, an adamantyl group, a norbornyl group, a tetrahydrofuran group, a polycyclic cycloalkyl group containing a norbornyl group having 10 to 30 carbon atoms, a phenyl group, a naphthyl group, a biphenyl group, an anthryl group, a phenanthrene group, a fluorenyl group, a pyrene group, a phenalene group, an indene group, a biphenylene group, a tetrahydronaphthyl group, and a dihydroanthryl group.

3. The photoacid generator according to claim 1, wherein $Y_1$ and $Y_2$ each independently represents any one selected from the group consisting of groups represented by the following formulas (1-a) to (1-i) and formulas (2-a) to (2-h) and (2-j) to (2-l):

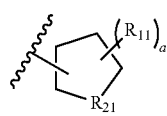
[Chemical Formula 1-a]

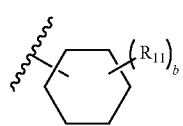
[Chemical Formula 1-b]

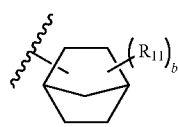
[Chemical Formula 1-c]

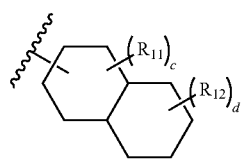
[Chemical Formula 1-d]

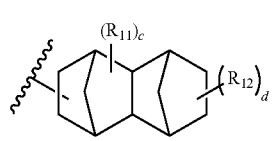
[Chemical Formula 1-e]

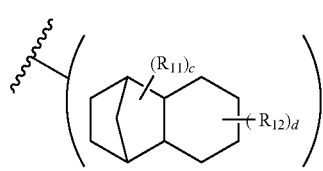
[Chemical Formula 1-f]

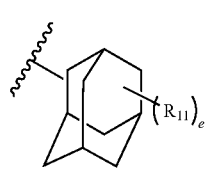
[Chemical Formula 1-g]

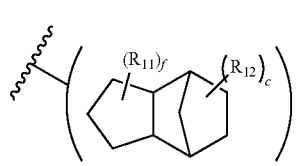
[Chemical Formula 1-h]

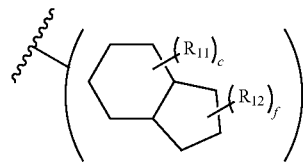
[Chemical Formula 1-i]

wherein in the formulas (1-a) to (1-i), $R_{11}$ and $R_{12}$ each independently represent any one selected from the group consisting of a hydrogen atom, an alkyl group, an alkoxy group, a perfluoroalkyl group, a perfluoroalkoxy group, a halogen atom, a hydroxyl group, a carboxyl group, a cyano group, a nitro group, an amino group, a thio group, a methylthio group, a methoxy group, OR', COR', COOR', O and S, while R' represents any one selected from the group consisting of an alkyl group and an aryl group;

$R_{21}$ represents any one selected from the group consisting of $CR_{24}R_{25}$, O, CO, S and $NR_{23}$; $R_{23}$ to $R_{25}$ each independently represent any one selected from the group consisting of a hydrogen atom, an alkyl group and an aryl group;

a, c and d each independently represent an integer from 0 to 9; b represents an integer from 0 to 11; e represents an integer from 0 to 15; f represents an integer from 0 to 7; and $0 \leq c+d \leq 17$, while $0 \leq c+f \leq 15$;

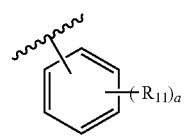
[Chemical Formula 2-a]

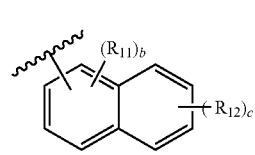
[Chemical Formula 2-b]

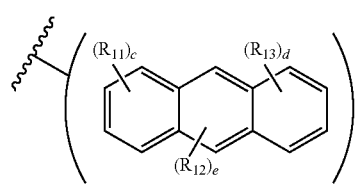
[Chemical Formula 2-c]

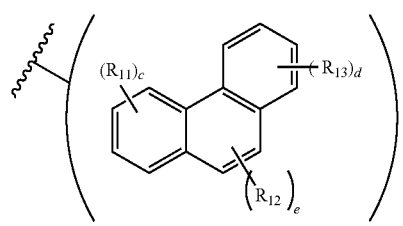
[Chemical Formula 2-d]

-continued

[Chemical Formula 2-e]

[Chemical Formula 2-f]

[Chemical Formula 2-g]

[Chemical Formula 2-h]

[Chemical Formula 2-j]

[Chemical Formula 2-k]

[Chemical Formula 2-l]

wherein in the formulas (2-a) to (2-h) and (2-j) to (2-l), $R_{11}$, $R_{12}$, $R_{13}$ and $R_{14}$ each independently represent any one selected from the group consisting of an alkyl group, an alkoxy group, a perfluoroalkyl group, a perfluoroalkoxy group, a halogen atom, a hydroxyl group, a cyano group, a nitro group, an amino group and a thio group;

$R_{21}$ and $R_{22}$ each independently represent any one selected from the group consisting of $CR_{24}R_{25}$, O, CO, S and $NR_{23}$; $R_{23}$ to $R_{25}$ each independently represent any one selected from the group consisting of a hydrogen atom, an alkyl group and an aryl group;

a, and h each independently represent an integer from 0 to 5; b represents an integer from 0 to 3; c and d each independently represent an integer from 0 to 4; e, f and g each independently represent an integer from 0 to 2; and $0 \leq c+d+e \leq 9$.

4. The photoacid generator according to claim 1, wherein the photoacid generator is any one selected from the group consisting of compounds represented by the following formulas (3-1), (3-2), (3-4) to (3-13):

[Chemical Formula 3-1]

[Chemical Formula 3-2]

[Chemical Formula 3-4]

[Chemical Formula 3-5]

[Chemical Formula 3-6]

[Chemical Formula 3-7]

[Chemical Formula 3-8]

[Chemical Formula 3-9]

[Chemical Formula 3-10]

[Chemical Formula 3-11]

[Chemical Formula 3-12]

[Chemical Formula 3-13]

5. A method for producing a photoacid generator, the method comprising:
   a first step of allowing a hydroxysulfonic acid salt to react with oxirane, and thereby producing a hydroxyethoxysulfonic acid salt;
   a second step of allowing the hydroxyethoxysulfonic acid salt produced above to react with a carbonyl halide and thereby producing an intermediate; and
   a third step of subjecting the intermediate thus produced to a substitution reaction of the cation, and thereby producing a compound represented by the following formula (1):

[Chemical Formula 1]

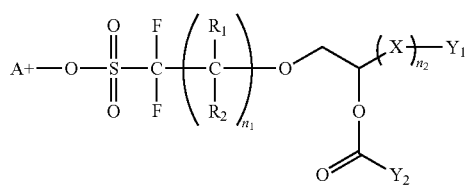

wherein in the formula (1),
- $Y_1$ and $Y_2$ each independently represent any one selected from the group consisting of a cycloalkyl group, a heterocycloalkyl group, an aryl group and a heteroaryl group;
- X represents any one selected from the group consisting of an alkanediyl, an alkenediyl, NR', S, O, CO and combinations thereof; R' represents any one selected from the group consisting of a hydrogen atom and an alkyl group;
- $R_1$ and $R_2$ each independently represent any one selected from the group consisting of a hydrogen atom, an alkyl group, an alkoxy group, a perfluoroalkyl group, a perfluoroalkoxy group, a halogen atom, a hydroxyl group, a carboxyl group, a cyano group, a nitro group, an amino group and a thio group;
- $n_1$ represents an integer or 1 or 2;
- $n_2$ represents an integer from 0 to 5; and
- $A^+$ represents an organic counterion.

6. The method for producing a photoacid generator according to claim 5, wherein the hydroxysulfonic acid salt is represented by the following formula (6), the oxirane is represented by the following formula (7), the hydroxyethoxysulfonic acid salt is represented by the following formula (8)

the carboxyl halide is represented by the following formula (9), and the intermediate is represented by the following formula (10):

[Chemical Formula 6]

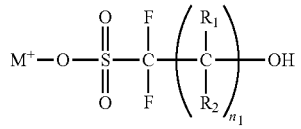

[Chemical Formula 7]

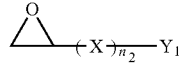

[Chemical Formula 8]

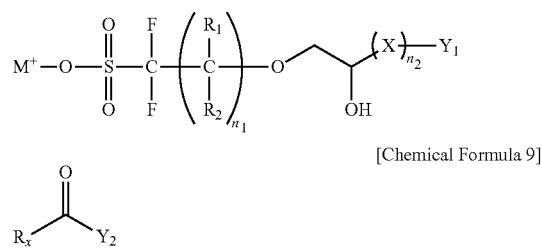

[Chemical Formula 9]

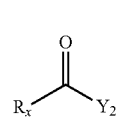

[Chemical Formula 10]

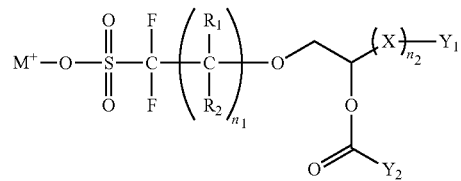

wherein in the formulas (6) to (8),
- $Y_1$ and $Y_2$ each independently represent any one selected from the group consisting of a cycloalkyl group, a heterocycloalkyl group, an aryl group and a heteroaryl group;
- X represents any one selected from the group consisting of an alkanediyl, an alkenediyl, NR', S, O, CO and combinations thereof; R' represents any one selected from the group consisting of a hydrogen atom and an alkyl group;
- $R_1$ and $R_2$ each independently represent any one selected from the group consisting of a hydrogen atom, an alkyl group, an alkoxy group, a perfluoroalkyl group, a perfluoroalkoxy group, a halogen atom, a hydroxyl group, a carboxyl group, a cyano group, a nitro group, an amino group and a thio group;
- $R_x$ represents a halogen atom;
- $n_1$ represents an integer of 1 or 2;
- $n_2$ represents an integer from 0 to 5; and
- $M^+$ represents an alkali metal ion.

7. The method for producing a photoacid generator according to claim 5, wherein any one step selected from the group consisting of the first step, the second step and a combination thereof is carried out by allowing the reaction to occur in the presence of any one catalyst selected from the group consisting of an acidic catalyst and a basic catalyst.

8. The method for producing a photoacid generator according to claim 5, wherein the second step is carried out by allowing the hydroxyethoxysulfonic acid salt and a carbonyl halide to react for 1 to 12 hours at a temperature of 20° C. to 100° C.

9. A resist composition comprising the photoacid generator according to claim 1.

* * * * *